United States Patent
Obermiller et al.

(10) Patent No.: US 8,915,941 B2
(45) Date of Patent: Dec. 23, 2014

(54) FISTULA CLOSURE DEVICES AND METHODS

(75) Inventors: F. Joseph Obermiller, West Lafayette, IN (US); Charles W. Agnew, West Lafayette, IN (US); Steve Chen, Westfield, IN (US); James B. Hunt, Bloomington, IN (US)

(73) Assignees: Cook Medical Technologies LLC, Bloomington, IN (US); Cook Biotech Incorporated, West Lafayette, IN (US)

( * ) Notice: Subject to any disclaimer, the term of this patent is extended or adjusted under 35 U.S.C. 154(b) by 0 days.

(21) Appl. No.: 13/517,801

(22) Filed: Jun. 14, 2012

(65) Prior Publication Data

US 2012/0323271 A1 Dec. 20, 2012

Related U.S. Application Data

(60) Provisional application No. 61/496,618, filed on Jun. 14, 2011.

(51) Int. Cl.
*A61B 17/08* (2006.01)
*A61B 17/00* (2006.01)

(52) U.S. Cl.
CPC ... *A61B 17/0057* (2013.01); *A61B 2017/00641* (2013.01); *A61B 2017/00588* (2013.01)
USPC .......................................................... 606/213

(58) Field of Classification Search
USPC .................. 606/213, 214, 215, 216, 217, 218
See application file for complete search history.

(56) References Cited

U.S. PATENT DOCUMENTS

| | | | |
|---|---|---|---|
| 2,127,903 | A | 3/1938 | Bowen |
| 3,996,921 | A | 12/1976 | Neuwirth |
| 4,511,653 | A | 4/1985 | Play et al. |
| 4,981,465 | A | 1/1991 | Ballan et al. |

(Continued)

FOREIGN PATENT DOCUMENTS

| | | |
|---|---|---|
| EP | 0 894 474 | 2/1999 |
| WO | WO 93/16658 | 9/1993 |

(Continued)

OTHER PUBLICATIONS

Himpson, Rebecca C., et al. "Histological evidence for enhanced anal fistula repair using autologous fibroblasts in a dermal collagen matrix". Comparative Clinical Pathology, Apr. 2006, vol. 16, No. 1.

(Continued)

*Primary Examiner* — Jonathan W Miles
(74) *Attorney, Agent, or Firm* — Woodard, Emhardt, Moriarty, McNett & Henry LLP

(57) ABSTRACT

Described are methods and systems for treating fistulae and other passageways and openings in the body. In certain aspects, an anchored suture is provided that extends from at or near a first fistula opening and through a fistula tract toward a second fistula opening. Various modes of anchoring may be used in this regard including, in some modes, having the suture extend from a deployed anchoring member positioned in and/or around the first opening. The anchored suture, which has a more slender cross sectional dimension relative to the fistula tract through which it extends, is capable of receiving an optional fill substance therealong in the tract. A fill substance can be or include a variety of biodegradable and/or non-biodegradable objects and materials including flowable and non-flowable materials.

29 Claims, 11 Drawing Sheets

(56) References Cited

U.S. PATENT DOCUMENTS

| | | | |
|---|---|---|---|
| 5,192,302 | A | 3/1993 | Kensey et al. |
| 5,330,503 | A | 7/1994 | Yoon |
| 5,345,948 | A | 9/1994 | O'Donnell, Jr. |
| 5,374,261 | A | 12/1994 | Yoon |
| RE34,866 | E | 2/1995 | Kensey et al. |
| 5,514,158 | A | 5/1996 | Kanesaka |
| 5,522,840 | A | 6/1996 | Krajicek |
| 5,549,122 | A | 8/1996 | Detweilwer |
| 5,584,827 | A | 12/1996 | Korteweg et al. |
| 5,620,461 | A | 4/1997 | Van De Moer et al. |
| 5,628,762 | A | 5/1997 | Al-Tameem |
| 5,643,305 | A | 7/1997 | Al-Tameem |
| 5,733,337 | A | 3/1998 | Carr, Jr. et al. |
| 5,752,974 | A | 5/1998 | Rhee et al. |
| 5,755,791 | A | 5/1998 | Whitson et al. |
| 5,846,183 | A | 12/1998 | Chilcoat |
| 5,860,978 | A | 1/1999 | McDevitt et al. |
| 5,947,994 | A | 9/1999 | Louw et al. |
| 5,997,575 | A | 12/1999 | Whitson et al. |
| 6,270,515 | B1 | 8/2001 | Linden et al. |
| 6,296,632 | B1 | 10/2001 | Lusher et al. |
| 6,315,787 | B1 | 11/2001 | Tsugita et al. |
| 6,325,789 | B1 * | 12/2001 | Janzen et al. ............... 604/506 |
| 6,331,319 | B1 | 12/2001 | Badylak et al. |
| 6,375,989 | B1 | 4/2002 | Badylak et al. |
| 6,475,232 | B1 | 11/2002 | Babbs et al. |
| 6,569,081 | B1 | 5/2003 | Nielsen et al. |
| 6,638,312 | B2 | 10/2003 | Plouhar et al. |
| 6,666,892 | B2 | 12/2003 | Hiles et al. |
| 6,800,056 | B2 | 10/2004 | Targaglia et al. |
| 2003/0013989 | A1 | 1/2003 | Obermiller et al. |
| 2003/0051735 | A1 | 3/2003 | Pavcnik et al. |
| 2004/0064017 | A1 | 4/2004 | Cappiello et al. |
| 2005/0049626 | A1 | 3/2005 | Burgard |
| 2005/0070759 | A1 | 3/2005 | Armstrong |
| 2005/0090860 | A1 | 4/2005 | Paprocki |
| 2005/0155608 | A1 | 7/2005 | Pavcnik et al. |
| 2005/0159776 | A1 | 7/2005 | Armstrong |
| 2006/0015142 | A1 | 1/2006 | Malazgirt |
| 2007/0031508 | A1 | 2/2007 | Armstrong et al. |
| 2008/0004657 | A1 * | 1/2008 | Obermiller et al. ......... 606/213 |
| 2010/0249828 | A1 * | 9/2010 | Mavani et al. ............. 606/213 |

FOREIGN PATENT DOCUMENTS

| | | |
|---|---|---|
| WO | WO 97/41778 | 11/1997 |
| WO | WO 98/01088 | 1/1998 |
| WO | WO 98/22158 | 5/1998 |
| WO | WO 98/25637 | 6/1998 |
| WO | WO 98/56290 | 12/1998 |
| WO | WO 00/45691 | 8/2000 |
| WO | WO 00/74576 | 12/2000 |
| WO | WO 01/05942 | 1/2001 |
| WO | WO 02/062234 | 8/2002 |
| WO | WO 02/074192 | 9/2002 |
| WO | WO 03/002165 | 1/2003 |
| WO | WO 03/077657 | 9/2003 |
| WO | WO 2004/103187 | 12/2004 |
| WO | WO 2005/030035 | 4/2005 |
| WO | WO 2005/053617 | 6/2005 |
| WO | WO 2005/070489 | 8/2005 |
| WO | WO 2006/119256 | 11/2006 |
| WO | WO 2006/119256 A2 | 11/2006 |

OTHER PUBLICATIONS

Khairy, G. E. A., et al. "Percutaneous obliteration of duodenal fistula". J.R. Coll. Surg. Edinb., 45, Oct. 2000, 342-344.

Lisle, David A., et al. "Percutaneous Gelfoam Embolization of Chronic Enterocutaneous Fistulas: Report of Three Cases". Diseases of the Colon & Rectum, vol. 50, No. 2, Dec. 2006.

Maluf-Filho, F. et al. "Endoscopic Treatment of Esophagogastric Fistulae with an Acellular Matrix". Gastrointestinal Endoscopy, Elsevier, NL, vol. 59, No. 5, Apr. 2004, p. 151, XP004854594 abstract.

Miklos, J. R., et al. "Rectovaginal Fistula Repair Utilizing a Cadaveric Dermal Allograft". International Urogynecology Journal, 1999, vol. 10, No. 6, pp. 405-406.

Moore, Robert D., et al. "Rectovaginal Fistula Repair Using a Porcine Dermal Graft". Obstetrics & Gynecology, 2004, 104, 1165-1167.

Schultz D J et al: "Porcine small intestine submucosa as a treatment for enterocutaneous fistulas" Journal of the American College of Surgeons, College, Chicago, IL, US, vol. 194, No. 4, Apr. 2002, pp. 541-543.

Schwesinger, Wayne H., "Management of Persistent Fistula After Gastrectomy" on-line question (www.medscape.com), posted on May 14, 2002.

Shah, A. M., et al. "Bronchoscopic closure of bronchopleural fistula using gelfoam" abstract. Journal of Association of Physicians of India, 2004, vol. 52, No. JUIN, pp. 508-509.

Sheiman, Robert G., et al. "Percutaneous Treatment of a Pancreatic Fistula after Pancreaticoduodenectomy". J Vasc Interv Radiol, 2001, vol. 12, No. 4, pp. 524-526.

Shelton, Andrew A., et al., "Transperineal Repair of Persistent Rectovaginal Fistulas Using an Acellular Cadaveric Dermal Graft (AlloDerm)", Diseases of the Colon & Rectum, 2006, vol. 49, No. 9, pp. 1454-1457.

Wilson Gunn on behalf of unnamed party, Letter to The European Patent Office, Jan. 30, 2007, pp. 1-4.

* cited by examiner

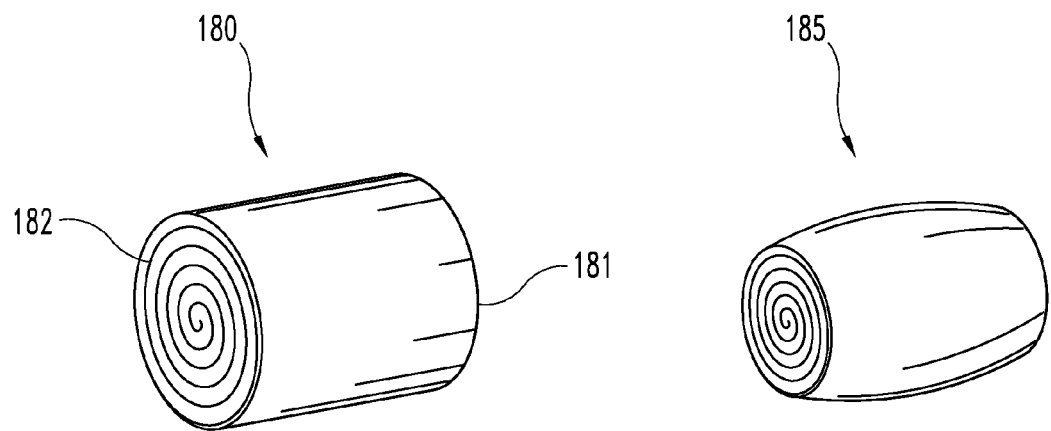
*Fig. 15A*  *Fig. 15B*
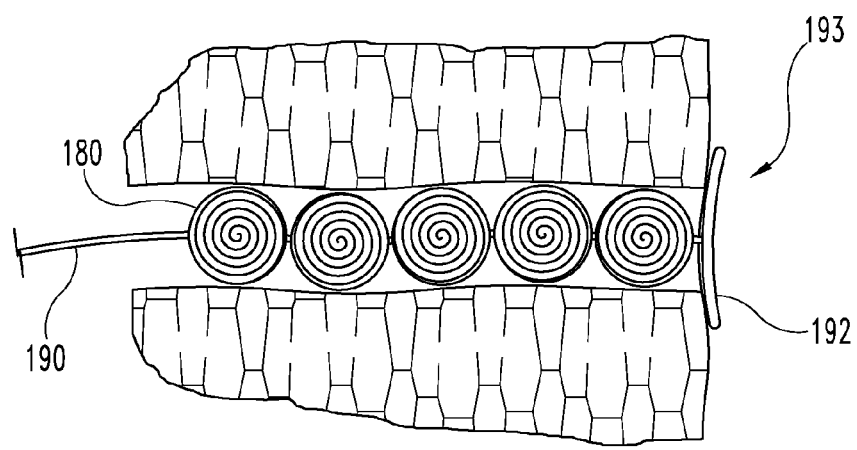
*Fig. 17*

FISTULA CLOSURE DEVICES AND METHODS

REFERENCE TO RELATED APPLICATION

This application claims the benefit of U.S. Provisional Application No. 61/496,618, filed Jun. 14, 2011, which is hereby incorporated by reference.

BACKGROUND

The present invention relates generally to medical technology and in particular aspects to methods and systems for addressing fistulae and other passageways and openings in the body. As further background, there exist a variety of passageways and openings in the body which can be plugged or otherwise occupied by medical implants and materials to provide benefit to the patient. For example, it may be desirable to plug or otherwise treat a fistula. A variety of fistulae can occur in humans. These fistulae can occur for a variety of reasons, such as but not limited to, as a congenital defect, as a result of inflammatory bowel disease, such as Chrohn's disease, irradiation, trauma, such as childbirth, or as a side effect from a surgical procedure. Further, several different types of fistulae can occur, for example, urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae.

Anorectal fistulae can result from infection in the anal glands, which are located around the circumference of the distal anal canal that forms the anatomic landmark known as the dentate line. Approximately 20-40 such glands are found in humans. Infection in an anal gland can result in an abscess. This abscess then can track through soft tissues (e.g., through or around the sphincter muscles) into the perianal skin, where it drains either spontaneously or surgically. The resulting void through soft tissue is known as a fistula. The internal or inner opening of the fistula, usually located at or near the dentate line, is known as the primary opening. Any external or outer openings, which are usually located in the perianal skin, are known as secondary openings.

A gastrointestinal fistula is an abnormal passage that leaks contents of the stomach or the intestine (small or large bowel) to other organs, usually other parts of the intestine or the skin. For example, gastrojejunocolic fistulae include both entero-cutaneous fistulae (those occurring between the skin surface and the intestine, namely the duodenum, the jejunum, and the ileum) and gastric fistulae (those occurring between the stomach and skin surface). Another type of fistula occurring in the gastrointestinal tract is an enteroenteral fistula, which refers to a fistula occurring between two parts of the intestine. Gastrointestinal fistulae can result in malnutrition and dehydration depending on their location in the gastrointestinal tract. They can also be a source of skin problems and infection. The majority of these types of fistulae are the result of surgery (e.g., bowel surgery), although sometimes they can develop spontaneously or from trauma, especially penetrating traumas such as stab wounds or gunshot wounds. Inflammatory processes, such as infection or inflammatory bowel disease (Crohn's disease), may also cause gastrointestinal fistulae. In fact, Crohn's disease is the most common primary bowel disease leading to enterocutaneous fistulae, and surgical treatment may be difficult because additional enterocutaneous fistulae develop in many of these patients postoperatively.

When surgery is deemed necessary, one operation for fistula closure is resection of the fistula-bearing segment and primary end-to-end anastamosis. The anastomosis may be reinforced by greater omentum or a serosal patch from adjacent small bowel. Still other methods for treating fistulae involve injecting sclerosant or sealant (e.g., collagen or fibrin glue) into the tract of the fistula to block the fistula. Closure of a fistula using a sealant is typically performed as a two-stage procedure, including a first-stage seton placement and injection of the fibrin glue several weeks later. This allows residual infection to resolve and to allow the fistula tract to "mature" prior to injecting a sealant. If sealant or sclerosant were injected as a one-stage procedure, into an "unprepared" or infected fistula, this may cause a flare-up of the infection and even further abscess formation.

There remain needs for improved and/or alternative devices and methods for addressing fistulae and other passageways and openings in the body. The present invention is addressed to those needs.

SUMMARY

The present invention provides, in certain aspects, unique methods and systems for treating fistulae and other passageways and openings in the body. A fistula to be treated might have a first opening, a second opening and a fistula tract extending therebetween, and in one illustrative method, an anchored elongate member is provided proximate the first fistula opening and extending therefrom through the fistula tract toward the second fistula opening. The anchored member is capable of receiving one or more plug bodies therealong for filling a substantial portion of the tract. Accordingly, in some instances, one or more plug bodies will be delivered into the fistula tract along the anchored member. In some modes, one or more plug bodies will be threaded over the anchored member, for example, for directly guiding and advancing the plug bodies into the tract. The delivery of a plug or other substance or material into the fistula tract may or may not involve the use of a separate delivery instrument that is configured to track along the elongate member. The elongate member can be anchored in a variety of manners. In some forms, anchoring of the elongate member might involve the deployment of an anchoring member proximate the first fistula opening with the elongate member extending from the anchoring member through the fistula tract and toward a secondary opening. As discussed herein below, an anchoring member of this sort can be shaped and configured in a variety of fashions, and there are a number of ways in which it can interact with tissue structures in and around the fistula. Some anchoring members will successfully cover the first fistula opening and/or lodge within the opening, potentially sealing off this opening. These and other anchoring members, in some aspects, will be adapted to at least partially embed into tissue adjacent the first fistula opening. In some instances, the elongate anchored member, which is capable of receiving one ore more plug bodies therealong in the fistula tract, itself will be an elongate three-dimensional graft member which may or may not have the capacity to expand inside the tract.

In another embodiment, the invention provides a method for treating a void that extends through soft tissue of a patient where the void includes a first opening, a second opening and a passageway that extends therebetween. As part of this method, an elongate three-dimensional graft member is made to extend through the passageway with a fill material received around and/or otherwise along the graft member and filling a substantial portion of the passageway. In some embodiments, the fill material will include multiple plug bodies that are received over the three-dimensional graft member.

In still another embodiment, the invention provides a method for treating a void such as that described above. In one step, an elongate guiding member is provided extending through the passageway. In another step, a first elongate plug body is advanced into the passageway along the guiding member. In yet another step, a second elongate plug body is advanced into the passageway along the guiding member which causes the first elongate plug body to move through the passageway toward the second opening. In doing so, the second elongate plug body may or may not directly contact the first elongate plug body. Further, the first elongate plug body and the second elongate plug body may or may not be connected to one another.

One aspect of the present invention provides a medical product for treating a void such as that described above. This particular product comprises an elongate three-dimensional graft member which has a first end, a second end and a length sufficient to traverse a substantial portion of the passageway. The product further includes two or more plug bodies that are coupled to and extend along the graft member between the first end and the second end of the graft member.

Another aspect of the present invention provides a medical product for treating a void such as that described above. This particular product comprises a guiding member and two or more plug bodies that are coupled to the guiding member. The guiding member has a first end, a second end and a length sufficient to traverse a substantial portion of the passageway. The two or more plug bodies are translatable along the guiding member in succession in between the first end and the second end of the guiding member. In a preferred product, at least one of the two or more plug bodies will comprise a remodelable extracellular matrix material, and the guiding member will extend through an opening occurring within each of the two or more plug bodies. Alternatively, a separately formed structure that provides an opening for receipt of the guiding member might be attached or otherwise incorporated onto the exterior of each of the two or more plug bodies.

Still another aspect of the invention provides an implantable medical device which comprises an implant body having a reinforced lumen extending therethrough. The implant body comprises a first material which forms a wall of the reinforced lumen, and a second material that is positioned around the reinforced lumen and is effective to volumetrically expand at an implant site so as to provide a volumetrically expanded mass of the second material around the reinforced lumen at the implant site. The first material, in some forms, will be provided by a hollow tubular structure that is formed separately from and embedded in the second material. The first material might also be a coating material that is applied to the second material. In one preferred embodiment, the second material is a remodelable ECM material.

A further embodiment of the invention provides a medical product for treating a fistula which includes a fistula tract extending from a fistula opening. This particular product includes a fillable member that is positionable over the fistula opening and includes a first side and a second side. The first side is configured to face away from the fistula opening, and the second side is configured to face the fistula opening and contact tissue around the fistula opening. The inventive product further includes an elongate pulling member that is configured to extend away from the second side of the fillable member and into the fistula tract when the fillable member is positioned over the fistula opening. The pulling member is coupled to the fillable member such that pulling the pulling member generally away from the fistula opening when the fillable member is positioned over the fistula opening pulls the first side of the fillable member toward the second side of the fillable member so as to force the second side of the fillable member against the tissue around the fistula opening for closing off the opening. The pulling member can be connected to the first side and/or the second side of the fillable member.

Yet another embodiment of the present invention provides a method for treating a fistula which comprises delivering a closure member to a fistula opening in a deformed first condition, and thereafter deploying the closure member in the fistula opening. In doing so, the closure member grasps tissue around the fistula opening and urges the opening toward a closed position as it transforms from the first condition to a deployed second condition.

Another inventive medical product includes an elongate plug body that provides an opening through which a guiding member can be received for advancing the plug body along the guiding member to a site within a patient. The plug body has a first end, a second end and an exterior side wall. The opening for receipt of the guiding member is located proximate the exterior side wall of the plug body. In some forms, the opening will be located in a peripheral region of the plug body. In some other forms, the opening will be incorporated onto the exterior side wall of the plug body, e.g., provided by a sleeve attached to the exterior side wall of the plug body.

Another aspect of the present invention provides a fistula plug that includes a plurality of three-dimensional plug bodies which are generally held together in succession to provide an elongate graft member for subsequent implantation in the body of a patient.

Another embodiment of the invention provides a fistula plug that includes an elongate three-dimensional graft member which provides an inner core. The fistula plug further includes a plurality of plug bodies which each have an opening through which the inner core can be received. The plug bodies are received over the inner core and reside adjacent one another in succession along the inner core such that the plurality of plug bodies extend over a substantial length of the inner core.

Other objects, embodiments, forms, features, advantages, aspects, and benefits of the present invention shall become apparent from the detailed description and drawings included herein.

BRIEF DESCRIPTION OF THE DRAWINGS

FIG. 15A is a perspective view of an illustrative graft element.

FIG. 15B is a perspective view of another illustrative graft element.

FIG. 17 is a partial view of a medical system according to another embodiment of the present invention.

DETAILED DESCRIPTION

Figure 1:
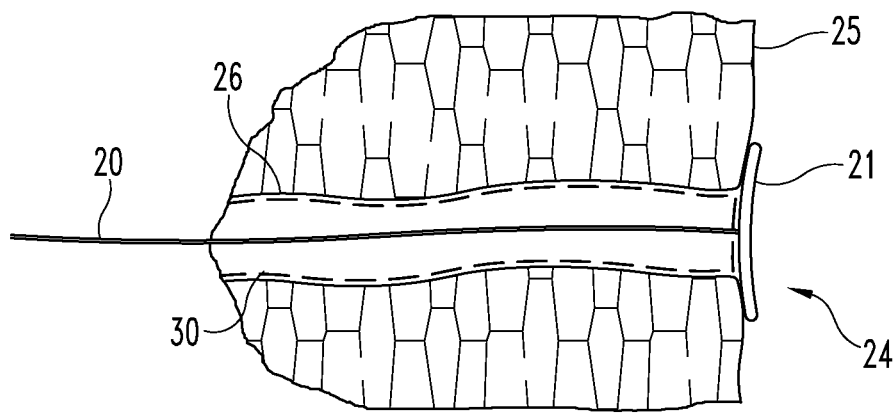
FIG. 1 is a partial view of a medical system according to one embodiment of the present invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique methods and systems for treating fistulae and other passageways and openings in the body. When directed to a fistula, this fistula might have a first opening, a second opening and a fistula tract extending therebetween, and in certain inventive embodiments, an anchored suture or other similar anchorable member having a relatively slender profile will be provided that extends from at or near the first fistula opening and through the fistula tract toward the second fistula opening. When it is a suture being anchored, the suture may be bonded or directly joined to tissues around the fistula, for example, by looping the suture through and around tissue at or near an opening to the fistula. Additionally or alternatively, the suture, cord, filament, plug-like core, etc. or other relatively thin-bodied elongate structure may extend from a deployed anchoring member. Any suitable anchoring device or adaptation may be utilized in this regard to at least help anchor the suture in place. Some of these anchoring devices will be designed to penetrate into surrounding tissues and others will not. In some instances, in addition to providing an anchoring function at a treatment site, an anchoring member will serve one or more additional functions there. For example, an anchoring member might also be effective to temporarily or permanently cover, plug, block, fill, close or similarly affect a fistula passageway or opening, or any segment thereof, by virtue of its presence in and/or around the fistula. Additionally, when this sort of anchored suture has a free end that extends toward the second opening, and potentially through the second opening, this free end might be left to freely hang in the fistula tract or it might be anchored to tissue at or near the second opening and/or connected to an anchoring member positioned at or near the second opening.

With reference now to FIG. 1, shown is an anchored suture 20 according to one embodiment of the present invention. In this illustrative arrangement the suture is coupled to, and extends away from, an anchoring body 21 that is positioned over a fistula opening 24 occurring in a wall 25 of a bodily structure. In doing so, the suture extends through a fistula tract 26 and toward a second fistula opening (not shown). While suture material, in particular, will be useful in certain inventive embodiments, as discussed elsewhere herein, a variety of other elongate materials and objects capable of being anchored can be used as an alternative to, or in addition, to suture material. These include various biodegradable and non-biodegradable cords, filaments, chains, strings, wires and other similar objects having relatively slender profiles for extending through a fistula tract or other passageway or void in patient tissue.

Continuing with FIG. 1, the anchoring body 21 is generally disc-shaped and is sized for contacting portions of the wall 25 adjacent opening 24 so as to inhibit its passage through the fistula opening. Body 21 can be formed with one or more of a variety of biodegradable and/or non-biodegradable materials as discussed elsewhere herein. In some preferred forms, the anchoring body is configured to at least partially block off fluid flow through the opening, and in some instances, to essentially seal off the opening from the passage of fluid. In some cases, holding anchoring body 21 in place over the fistula opening will be accomplished, at least in part, by applying tension to suture 20 and generally maintaining this tension. Additionally or alternatively, anchoring body 21 can be bonded or otherwise attached to tissue around the opening, and in some forms, incorporate barbs or other adaptations to penetrate into tissue around the fistula to at least help hold the anchoring body in place. Further, in instances where it is necessary or desirable to deliver anchoring body 21 through the fistula tract from the second opening, the body can be made compressible or otherwise deformable, for example, so that it can be folded, rolled, collapsed and/or otherwise compacted to a lower-profile condition for traversing the tract.

When an anchoring member relies, at least in part, on its size and shape to inhibit its passage through a bodily opening, this sort of member can be shaped and configured in a variety of manners. These include but are not limited to various three-dimensional shapes having rectilinear and/or curvilinear portions. Suitable three-dimensional rectilinear shapes can have any suitable number of sides, and can include, for example, cubes, cuboids, tetrahedrons, prisms, pyramids, wedges, and variations thereof. Suitable three-dimensional curvilinear shapes can include, for example, spheres, spheroids, ellipsoids, cylinders, cones, and any suitable variations thereof (e.g., a segment of a sphere, or a truncated cone, etc.). These and other anchoring members when used in the present invention can be formed with one or more of a variety of biodegradable and/or non-biodegradable materials as discussed elsewhere herein.

Continuing with FIG. 1, the anchored suture, which has a more slender cross sectional dimension relative to the fistula tract through which it extends, is capable of receiving an optional fill substance 30 therealong in the tract. Fill substance 30 can be or include a variety of biodegradable and/or non-biodegradable objects and materials as discussed elsewhere herein including flowable and non-flowable materials and objects. In some instances, the anchored suture will aid in the delivery of a fill substance into the fistula tract such as where a three-dimensional plug or plug-type device, or a separate delivery instrument carrying such a device, is specifically adapted to track along the suture inside the tract. In some modes, the anchored suture will be threaded through an opening in or on a deliverable object for directly guiding and advancing that object into the tract. Optionally, the second fistula opening can be fully or partially closed off following the delivery of a fill substance into the tract.

In some instances, the fill substance 30 will reside in the tract for a relatively short period of time such as where the fill substance is an aqueous medium (e.g., an antimicrobial mixture) that is used to flush the tract, optionally followed by the introduction of one or more other fill substances or devices into the tract. In some other embodiments, steps will be taken so that a fill material remains in the tract for a somewhat lengthier period of time, in some cases indefinitely. This might involve blocking off or closing a fistula opening so that a fill device or material is prohibited from passing through the opening. Illustratively, a fistula tract can be filled with a flowable material, and opposite ends of the tract can be closed off so that the flowable material remains essentially trapped there. In some aspects, a capping member will be used in this regard to cap off a fistula opening, and this capping member will optionally incorporate an access port that provides access through the capping member for supplying additional fill material to the tract as needed or desired.

Suitable fill substances include various space filling materials such as remodelable or resorbable materials, for example, a comminuted, fluidized, and/or gelatinous remodelable material as described elsewhere herein, or other substances (e.g., in the form of fluids, pastes, gels, sponges, powders, tissue fragments, segments, strips, layers, etc.), therapeutic agents, e.g. suitable drugs such as antibiotics, antimicrobial agents or the like. Other options include but are not limited to polymer, contrast medium, saline, a non-bioabsorbable material, collagen rods or particulates, a collagenous or gelatinous foam, air, chitosan, gelatin, oxidized regenerated cellulose, calcium alginate, alginate, thrombin-fibrin enhanced materials, fibrin glues, or any suitable combination thereof. As well, a plug or other material might be coated with one or more substances such as a drug coating, adhesive, sclerosant or the like.

An anchorable element such as a suture can be anchored in a variety of fashions including some that utilize glues or other bonding agents, tissue welding techniques, friction fitting or lodgment of an anchoring member, use of hooks, barbs, pins, single- and multiple part fasteners and/or other suitable anchoring modes as discussed elsewhere herein. In some instances, an anchoring system will include a deployed anchoring member that achieves at least some of its anchoring ability through penetration into tissue at or around a fistula opening. These types of devices can be shaped and configured in a variety of manners. With some designs, in addition to providing an anchoring function at a fistula treatment site, an anchoring device will serve one or more additional functions at the site such as temporarily or permanently covering, plugging, blocking, filling, closing or similarly affecting a bodily passageway or opening, or any segment thereof, by virtue of its presence in and/or around the passageway or opening.

Figure 2:
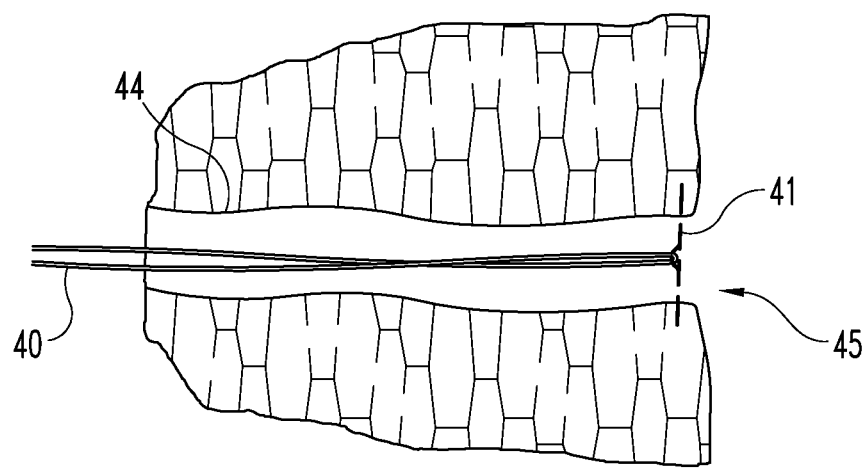
FIG. 2 is a partial view of another inventive medical system.

With reference now to FIG. 2, shown is an anchored suture 40 according to another embodiment of the present invention. In this illustrative system, an anchoring member 41 is deployed in a fistula tract 44 just inside a first fistula opening 45 with portions of the member penetrating into tissue around the tract. As discussed elsewhere herein, the anchoring member can be shaped and configured in a variety of manners for penetrating into tissues at the treatment site.

Penetrating and non tissue-penetrating anchoring members can be or include various types of frame and frame-like elements. These include single- and multiple-part devices. In some forms, a frame member will include a filament or wire body or other similar frame or frame-like support structure. Frame members, in some embodiments, can be designed to move between a first condition and one or more other conditions, for example, in the case of a frame that is compactable to a compacted, first condition, and when in this compacted condition, is then expandable to an expanded, second condition. In forms where a frame has the capacity to expand, these frames can include those that are considered self-expanding and those that require at least some manipulation in order to expand.

Frames of this sort and other similar support elements useful in the present invention can be constructed using one or more pieces of superelastic wire or any of a variety of other suitable materials described herein or otherwise known to those skilled in the art including MRI compatible materials. Frames and other similar expandable and non-expandable support members, when utilized in the present invention, may be made from metallic or non-metallic material, or both. The non-metallic material can suitably be a synthetic polymeric material, including for example bioresorbable and/or non-bioresorbable plastics. Materials commonly used in medical device construction include biologically compatible metals, e.g., stainless steel, titanium, tantalum, gold, platinum, copper and the like, as well as alloys of these metals; synthetic polymeric materials; low shape memory plastic; a shape-memory plastic or alloy, such as nitinol; and the like.

Continuing with FIG. 2, the suture 40 is threaded through an opening in the anchoring member 41 which allows opposite ends of the line to extend alongside one another through the tract 44 toward a second fistula opening (not shown). With this sort of doubled-up arrangement, if the suture is not otherwise attached to the anchoring member, it is possible to disassociate the suture from the anchoring member if the suture is no longer needed or desired at the treatment site. For example, the suture might be relied upon in the deployment of an anchoring member and/or other device or material at the treatment site, and then if it is no longer needed, it can be removed and discarded. In one preferred embodiment, such a suture will act like a guide wire to guide a plug or plug-type device, or a separate delivery instrument carrying such a device, along the suture line and into the tract. Thereafter, the suture (and delivery instrument if used) can be removed leaving the plugs behind in the tract. In some modes, one or both ends of the suture will be threaded through a longitudinal passage in a plug body for directly guiding and advancing the plug body into the tract over the suture.

In certain embodiments, the deployment of a frame or frame-like device in and/or around a fistula opening will be effective to reduce the size of that opening, for example, by grasping or otherwise contacting tissue around the opening and urging that tissue inwardly toward central regions of the opening. Illustratively, an inventive method can involve the delivery of a deformable closure member to a fistula opening in a deformed first condition, and thereafter deploying the closure member in the fistula opening. In doing so, the closure member, as it transforms from the first condition to a deployed second condition, will grasp tissue around the fistula opening and pull that tissue inwardly so as to urge the opening toward a relatively more closed position. Such deformable closure members can be delivered to treatment sites in a variety of manners. In some instances, a resilient closure member will be provided in a relaxed condition whereafter it can be deformed (e.g., collapsed, bent, folded, compressed, etc.) from this relaxed, first condition to a deformed, second condition and held there temporarily. In this deformed, second condition, the resilient member is then poised to essentially return to its relaxed, first condition. Illustratively, a closure member can be compressed into a compressed condition (e.g., by bending and/or folding portions of the member) for positioning in a delivery device lumen having a relatively smaller diameter than that which the member could otherwise fit in its relaxed condition. In this compressed condition, the member then has the ability to try to self-expand essentially back to its prior, relaxed condition upon being removed from the delivery device lumen. Other alternative closure members will be configured for receipt over a delivery member in a deformed condition for delivery to a treatment site. At the treatment site, these resilient members can then be pushed or otherwise forced off of the delivery instrument whereupon they will try to revert essentially back to their prior, relaxed condition.

Figure 3:
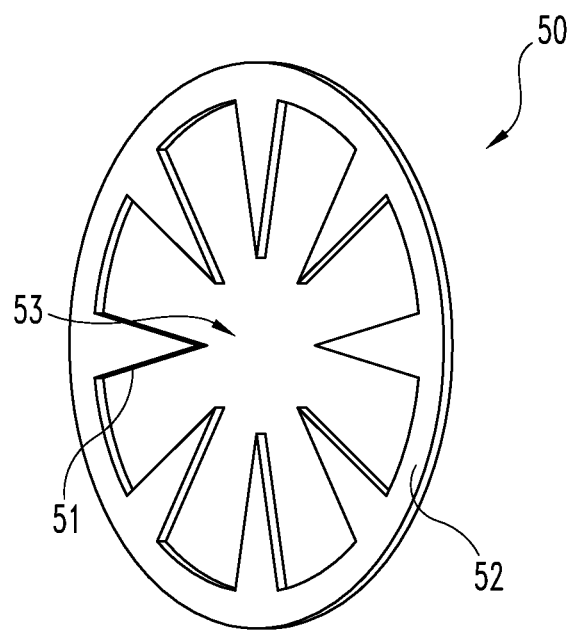
FIG. 3 is a perspective view of an inventive anchoring device.

Referring now to FIG. 3, shown is an anchoring member 50 according to one embodiment of the present invention. In a generally relaxed condition as shown, anchoring member 50 has an overall disc-like shape and includes a plurality of spaced tissue-penetrating members 51 that extend inwardly from and around a generally annular, outer portion 52. An open region 53 occurs inward of the annular portion and is defined by this portion and the plurality of tissue penetrating members. In an illustrative use, the resilient anchoring member 50 can be deformed to a deformed condition for delivery into and/or around a fistula. At a suitable deployment location, e.g., a primary fistula opening or a location with a fistula tract, the anchoring member can be released or otherwise deployed whereby it will attempt to return generally to its prior relaxed condition causing one or more of the tissue-penetrating members 51 to grasp and pull surroundings tissues as the member transforms from its delivery configuration to a deployed condition. In doing so, the tissue-penetrating members 51 will pull that tissue inwardly and urge the tissue opening, tract, etc. toward a relatively more closed position.

Figure 4A:
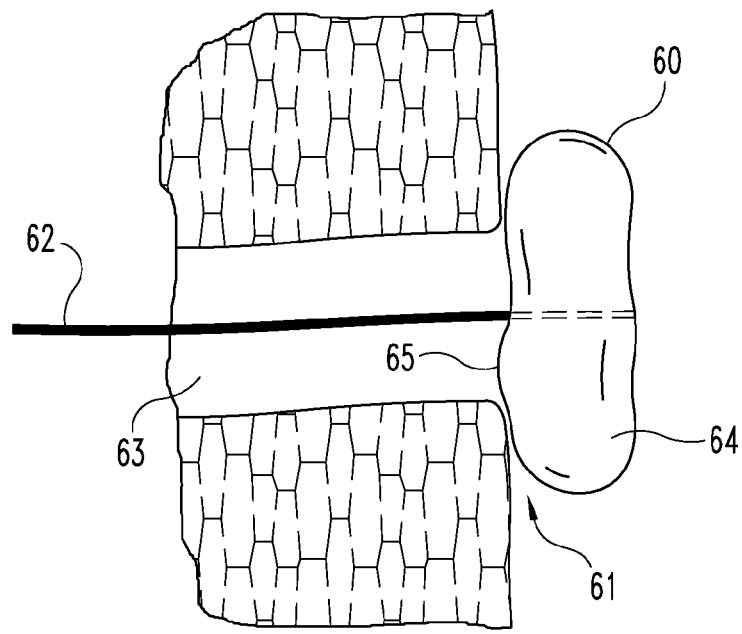
FIG. 4A is a partial view of another inventive medical system showing an illustrative anchoring member in a first condition.
Figure 4B:
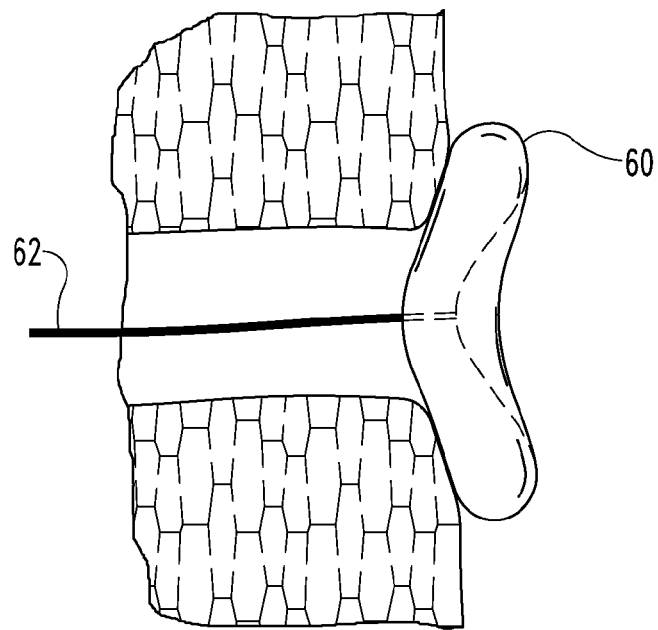
FIG. 4B shows the anchoring member of FIG. 4A in a second condition.

Continuing with alternative forms of anchoring-type devices, in some aspects of the present invention, a conformable and fillable body will be made to reside in and/or around a fistula tract or other passageway or opening in the body. Illustratively, an inventive treatment product can include a somewhat flexible, fillable member for positioning over a fistula opening, while further including an elongate pulling member for extending away from the fillable member and into a fistula tract when the fillable member is positioned over the fistula opening. In some forms, an anchoring member will be or include a fillable component. With reference now to FIG. 4A, shown is an illustrative fillable member 60 positioned over a fistula opening 61 with an elongate pulling member 62 extending from the fillable member and into a fistula tract 63. Fillable member 60 has a first side 64 facing generally away from the fistula opening, and a second side 65 generally facing the fistula opening and contacting tissue around the fistula opening. The pulling member is connected to the first side of the fillable member and passes through the second side of the fillable member for extending into the fistula tract. With this construction and placement in the fistula, the act of pulling the pulling member generally away from the fistula opening as shown in FIG. 4B is effective to pull the first side of the fillable member toward the second side of the fillable member which in turn forces the second side of the fillable member against the tissue around the fistula opening for closing off the opening. The fillable member can be partially or fully filled with any of the fill substances and materials discussed elsewhere herein.

A pulling member can be connected to a fillable member in a variety of fashions, with connection locations potentially occurring at one or more locations around and/or inside the fillable member. In some preferred forms, the pulling member will be coupled to the fillable member so that it can be pulled generally away from the fistula opening when the fillable member is positioned over the fistula opening, thereby causing the fillable member to at least somewhat conform to tissues around the fistula opening as it forcefully contacts those tissues. In some designs, such a fillable member will have a first side that is configured to face away from the fistula opening, and a second side that is configured to face the fistula opening and contact tissue around the fistula opening, and the pulling member will be coupled to the fillable member such that pulling the pulling member generally away from the fistula opening when the fillable member is positioned over the fistula opening pulls the first side of the fillable member toward the second side of the fillable member which directly or indirectly forces the second side of the fillable member against the tissue around the fistula opening for closing off the opening. In some preferred designs, the pulling member will be directly connected to the first side of the fillable member, for example, by passing through the second side of the fillable member. In some other preferred designs, an indirect connection between the pulling member and the first side of the fillable member will allow the pulling member to manipulate the first side.

Fillable bodies can be formed with a variety of biocompatible materials including but not limited to remodelable materials, e.g. absorbable synthetics or extracellular matrix materials, or non-absorbable synthetic materials, including those described herein. In certain aspects, suitable fillable members can be obtained by isolating tubular or pouch form ECM materials, such as, for example, small stomachs, urinary bladders, vascular vessels, ureters, and/or suitable portions of the gastrointestinal (GI) tract. Other suitable materials may include substantially non-antigenic elastic materials.

Figure 5:
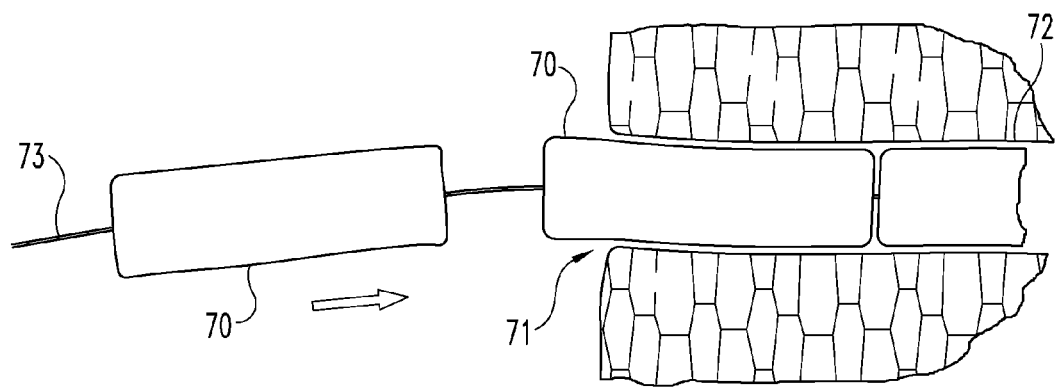
FIG. 5 is a partial view of another inventive medical system.

Continuing with additional types of fill constructs, materials and substances that can be introduced into a fistula tract or other bodily passageway, as discussed above, a variety of plugs and plug-type devices, or components thereof, can be delivered to such locations in the body. With reference now to FIG. 5, shown is an illustrative example of multiple plug bodies 70 being delivered through a fistula opening 71 and into a fistula tract 72 over an anchored line 73 which could be any of the anchored lines or other elongate objects described herein such as a small diameter plug-like core. While not necessary to broader aspects of the invention, in this particular embodiment, each of the plug bodies has a central longitudinal lumen through which the anchored line 73 extends for advancing the bodies over the line and into the tract. In some instances, it will be desirable to substantially fill the tract with one or more such plug bodies, and then to block or close off the fistula opening so as to impede the passage of the plug bodies back through the opening. By using multiple plug or plug-type device rather than a single plug body, it is possible to enhance certain delivery characteristics and treatment abilities of an overall plug arrangement at an implant site. Illustratively, in some forms, the multiple plug bodies 70 will be able to move in an articulating fashion while being delivered into the tract along the line, and also at the treatment site.

While the plug bodies in FIG. 5 are generally cylindrical, such plugs and other implants when utilized in the present invention can be shaped and configured in a variety of manners. These include various shaped, three-dimensional constructs, and even some sheet-like or generally two-dimensional implantable materials. When generally cylindrical, an implant body portion can, for example, have a diameter of about 0.5 mm to about 30.0 mm and a length of about 0.5 cm to about 30 cm, although larger or smaller values for these dimensions could be used in accordance with the invention. Thus, an implant in some forms of the invention will include a portion that is generally cylindrical, and has a diameter ranging from about 1.0 mm to about 18.0 mm, or from about 3.0 mm to about 12.0 mm, or from about 4.0 mm to about 8.0 mm, and a length ranging from about 2.0 cm to about 18.0 cm, or from about 4.0 cm to about 12.0 cm. As well, an implant body portion may be formed with one or more of a variety of biocompatible materials including some that are naturally derived and some that are non-naturally derived, as described elsewhere herein.

An implant body can have a constant or varying cross-sectional area along its length. Illustratively, an implant body, or any portion thereof, can exhibit a generally cylindrical shape, a conical shape or any other suitable shape including some that have tapered and/or non-tapered longitudinal portions. As well, a cross section of a particular portion of an implant body can exhibit a variety shapes including some that have rectilinear and/or curvilinear features. Thus, an implant body can include a portion having a generally circular or non-circular (e.g., elliptical, square, star-shaped, hexagonal, etc.) cross section. Additionally or alternatively, an implant body can include various other three-dimensional volumetric body portions such as but not limited to braids, tubes, hemi-cylinders, strands, threads, strips, pieces, slabs, wedges, blocks and other shaped body portions having suitable dimensions.

The implant bodies and other implant components described herein can be formed in any suitable manner including but not limited to by extrusion, using a mold or form, construction around a mandrel, and/or combinations or variations thereof. In some embodiments, an implant body is formed with a reconstituted or otherwise reassembled ECM material. Implant bodies can also be formed by folding or rolling, or otherwise overlaying one or more portions of one or more biocompatible materials, such as one or more layers of a biocompatible sheet material, for example, as shown in the rolled sheet members of FIGS. 15A and 15B. The overlaid biocompatible sheet material can be compressed and dried or otherwise bonded into a volumetric shape such that a substantially unitary construct is formed. In some forms, an inventive implant component is constructed by randomly or regularly packing one or more pieces of single or multilayer ECM sheet material within a mold and thereafter processing the packed material.

Figure 18:
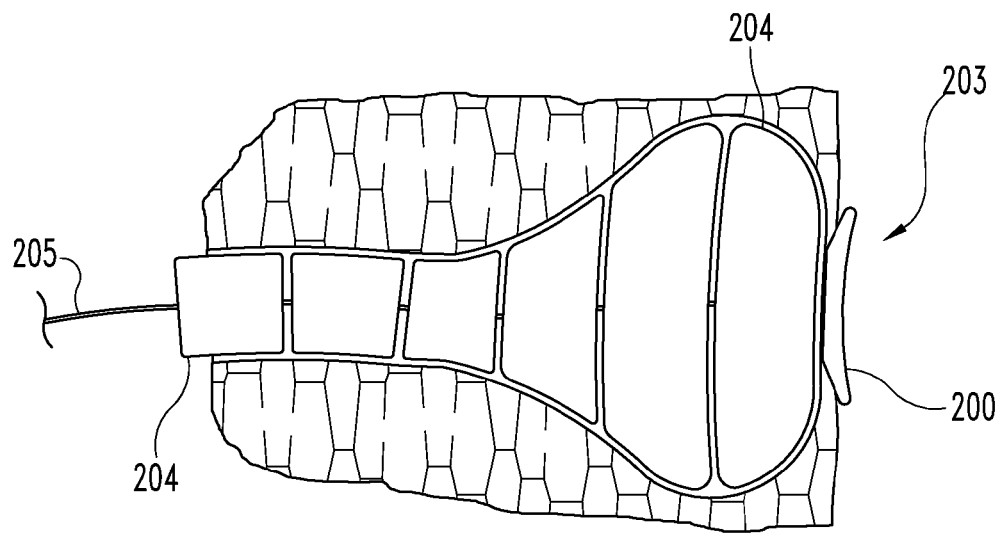
FIG. 18 is a partial, side view of another inventive medical system.

When more than one plug body is to be delivered to a treatment site, any one plug body can vary with respect to another plug body in terms of its size, shape, material(s) of construction and/or any other physical or other characteristic as described elsewhere herein. Illustratively, FIG. 18 shows a fistula treatment product that includes an anchoring member 200 for blocking or sealing off a primary fistula opening 203, and multiple plug bodies 204 that are received over a suture 205 that extends from the anchoring member toward a secondary fistula opening (not shown). In alternative forms, such a product will include a different anchoring member or no separate anchoring member.

Continuing with FIG. 18, spaces and regions within a fistula can exhibit any number of shapes or irregularities. In some instances, regions near a primary opening will be more voluminous than other fistulous regions such as those that are closer to a secondary fistula opening, for example, due to a laterally-expanding abscess that has formed at or near the primary opening. In accordance with certain aspects of the present invention, having expandable and/or non-expandable graft bodies occupying different volumes within a single graft product can help accommodate these situations. In FIG. 18, graft bodies nearer the primary opening 203 are wider or more voluminous for filling or attempting to fill the larger fistulous spaces near the primary opening. Extending away from the primary opening, the graft bodies are less wide or less voluminous to account for the smaller fistulous spaces there. This sort of combination produces an overall graft product that is somewhat tapered along its longitudinal axis. In some preferred embodiments, a graft body will be expandable upon delivery to occupy a fistulous volume such as those shown in FIG. 18. In some aspects, a multi-body arrangement will be formed prior to delivering the product to an implant site as described elsewhere herein, while in other aspects, a collection of graft bodies will be formed, at least in part, at the implant site. This sort of strand can include any suitable number of segments, and there can be multiple strands placed along a bodily passageway or tract.

Additionally, if two plug bodies include raw material(s) of essentially the same kind, material in one of the plug bodies might be physically, chemically, biologically and/or otherwise modified during construction of the body. Accordingly, specific types of plug bodies can be placed at particular locations along the overall graft, and in this regard, the location of a particular type of plug body might be selected based on advantages expected to result from having that plug body reside at a particular location at the eventual treatment site (e.g., at or near a fistula opening or at any other specific location in a fistula or other bodily passageway or opening). As one example, plug bodies within a single graft device can have different densities, rates of degradation, degrees of stiffness, resistances to hydration, abilities to withstand exposures to certain substances at an implant site, and/or can be different with respect to any other quality including being coated with or otherwise incorporating one or more substances such as drugs (antimicrobial, anti-inflammatory, etc.), bioactive substances, radiopaque components and/or other substances as described elsewhere herein. Illustratively, a graft might include some plug bodies that are formed with a naturally derived material such as a harvested ECM material and other segments that are formed with a non-naturally derived material such as a biodegradable synthetic polymeric material. In some forms, a naturally derived material and a non-naturally derived material will be used in the formation of a single plug body within a larger inventive graft. As another example, a graft might include some ECM plug bodies of a certain density and thus potentially helpful for plugging or sealing purposes, and also some other ECM segments of a relatively less density and thus potentially more receptive to tissue ingrowth and better for incorporation purposes. While such combinations will certainly be useful in some applications, it is merely illustrative of the many possible plug body combinations falling within the scope of some aspects of the present invention.

Figure 6:
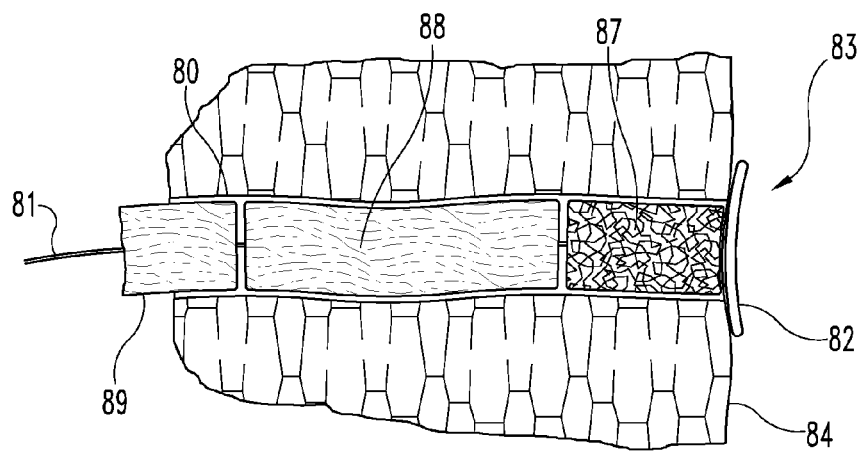
FIG. 6 is a partial view of still another inventive medical system.

With reference now to FIG. 6, shown is an illustrative treatment system that includes multiple plug bodies positioned in a fistula tract 80 over an anchored guiding member 81 (e.g., a suture line). The guiding member is connected to, and extends away from, an anchoring body 82 that is positioned over a fistula opening 83 occurring in a wall 84 of a bodily structure. In doing so, the guiding member extends through the fistula tract 80 and toward a second fistula opening (not shown). The anchoring body 82 contacts tissue of the wall 84 around the fistula opening 83, and it is sized and physically constructed so as to provide anchoring support to the guiding member at the fistula opening. Body 82 can be constructed in various forms as described herein, and in some preferred embodiments, its construction will enable it to at least partially block off the opening, and in some instances, to essentially seal off the opening. In some instances, such multi-plug products will be constructed prior to delivering them to an implant site, and in these instances, the plug bodies may or may not be directly connected to one another. In some other instances, a multi-plug arrangement like that shown in FIG. 6 will be formed, at least in part, at an implant site.

In this particular embodiment, the group of plug bodies includes a first plug body 87, a second plug body 88 and a third plug body 89 (partially shown), and in this regard, FIG. 6 is at least illustrative of how any two plug bodies in a multiple plug body system can be different from one another in terms of their size, shape and/or other characteristics as described elsewhere herein, and how plug bodies of a particular type might be chosen to reside in a particular location in a fistula tract or other bodily passageway or opening. In this case in particular, the first plug body 87 is more dense and also somewhat shorter than the second plug body 88. While such a combination will certainly be useful in some applications, it is merely illustrative of the many possible plug combinations falling within the scope of the present invention when more than one plug body is utilized at a treatment site. In some instances, a fistula tract or other treatment site will be mapped or otherwise analyzed prior to receiving one or more plug bodies therein, and the number of plug bodies and their individual qualities will be selected based on this analysis, for example, to optimize healing in different regions or zones of a fistula tract based on an initial analysis or estimate. Illustratively, a multi-plug arrangement for treating a fistula might have a first plug body at or near a primary fistula opening with subsequent plug bodies gradually decreasing in size, width, volume, etc. so that, for example, the overall multi-plug arrangement will exhibit somewhat of a taper.

When a device is specifically adapted for tracking along a suture of other guiding element, in some forms, the device itself will provide a lumen or opening through which the guiding member can be received for delivery and/or other purposes. In the case of a plug body, for example, this sort of feature may be obtained by attaching another object or material to a plug body so that a lumen or opening is thus formed along an exterior surface of the plug body. In some preferred forms, a separate element having a pre-formed opening or pathway will be incorporated onto a plug body. In some other preferred forms, a lumen or other passageway will extend through a portion of the plug body, for example, where a centrally- or non-centrally located lumen extends through the body of an elongate or other plug member. Such a lumen may be formed during the initial construction of the plug body (e.g., when constructing a plug body in a mold), or it may be made subsequently by removing an amount of material from an already-formed plug body so as to form a lumen through the plug body.

In some forms, there will be a lumen or other passageway in a plug body, and a wall of the lumen will be formed of a different material than other regions of the plug body. Illustratively, an implant body may include a first material which forms a wall of an internal lumen, and a second material that is positioned around this lumen. The degree of similarity or dissimilarity between the first and second materials can vary. In some forms, the first material and the second material initially have the same basic composition, but the first material is treated or otherwise modified to provide reinforcement to a wall of the lumen. Alternatively, for example, the first material and the second material may have quite different compositions from the start such as where the first material includes a resorbable synthetic material and the second material includes a non-synthetic material. Various combinations of the materials described herein may be used.

Figure 7A:
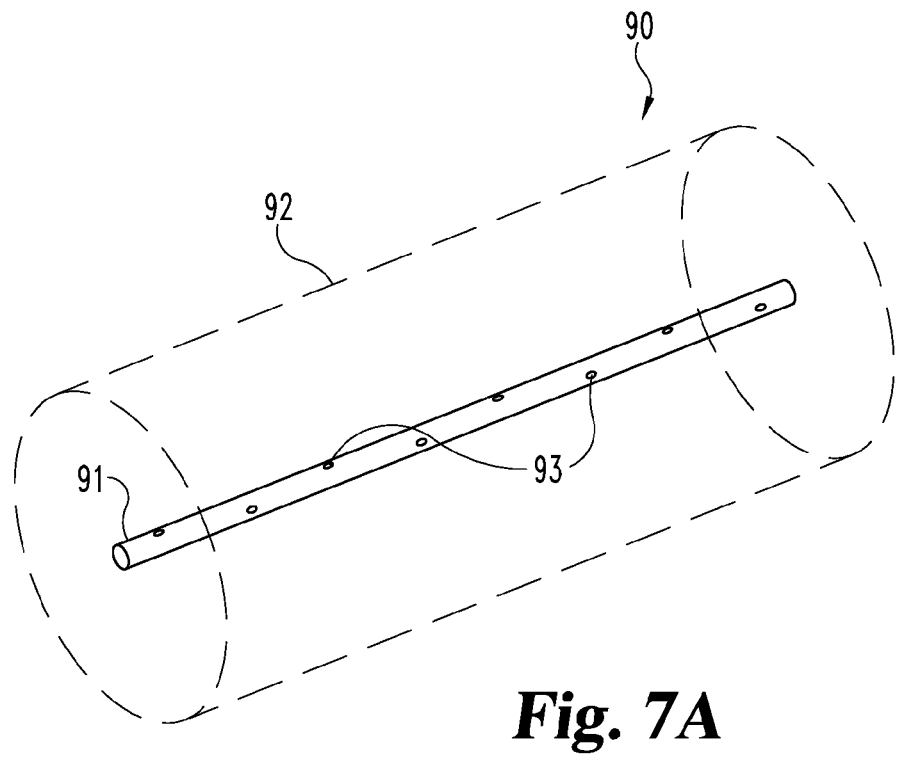
FIG. 7A is a perspective view of an inventive implantable device.
Figure 7B:
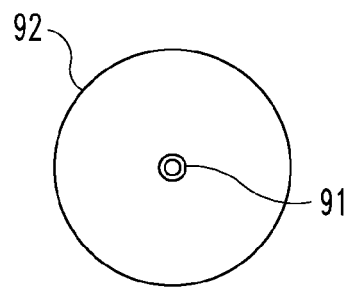
FIG. 7B is an end view of the implantable device of FIG. 9A.

FIG. 7A provides a perspective view, and FIG. 7B provides an end view, of an illustrative plug device 90 having an overall generally cylindrical shape. Device 90 includes a hollow, tubular insert 91 that is embedded within a body 92 of a volumetrically expandable, first material. Tubular insert 91 is formed with a lesser or non-expandable, second material, and its walls provide a passageway that traverses body 92. Optionally, multiple spaced openings 93 may be present in the side wall of the insert. When the inside of the tubular insert is accessed for hydration purposes, hydration can be achieved with any suitable liquid, typically an aqueous medium such as sterile water, saline, or the like. The wetting medium may also include other therapeutic substances, such as antibiotics, anesthetics and/or other pharmaceuticals. Additional sterilization steps can also be performed through the tubular insert. Body 92 is effective to volumetrically expand at an implant site so as to provide a volumetrically expanded mass of the first material around the second material at the implant site.

Figure 8:
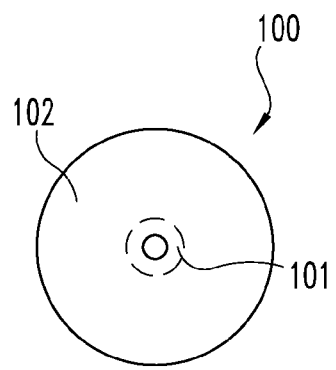
FIG. 8 is an end view of another inventive implantable device.

With reference now to FIG. 8, shown is an end view of an inventive plug device 100 according to another aspect of the invention. In this specific illustrative embodiment, a plug device 100 has an overall shape similar to that of the device in FIG. 7A although it could be shaped and configured in a variety of other manners as discussed elsewhere herein. A central lumen extends through the device as shown. An inner plug region 101 including a first material provides walls of the lumen, and an outer plug region 102 including a second material surrounds the inner plug region 101. In some preferred forms, a single material initially forms all regions of the plug body, and a physical, chemical and/or other modification to select portions of that material produces the differing first and second materials. Illustratively, a fluid treatment can be applied to select portions of a material to alter certain material properties of those portions such as their density, porosity, bioactivity, etc.

Figure 9A:
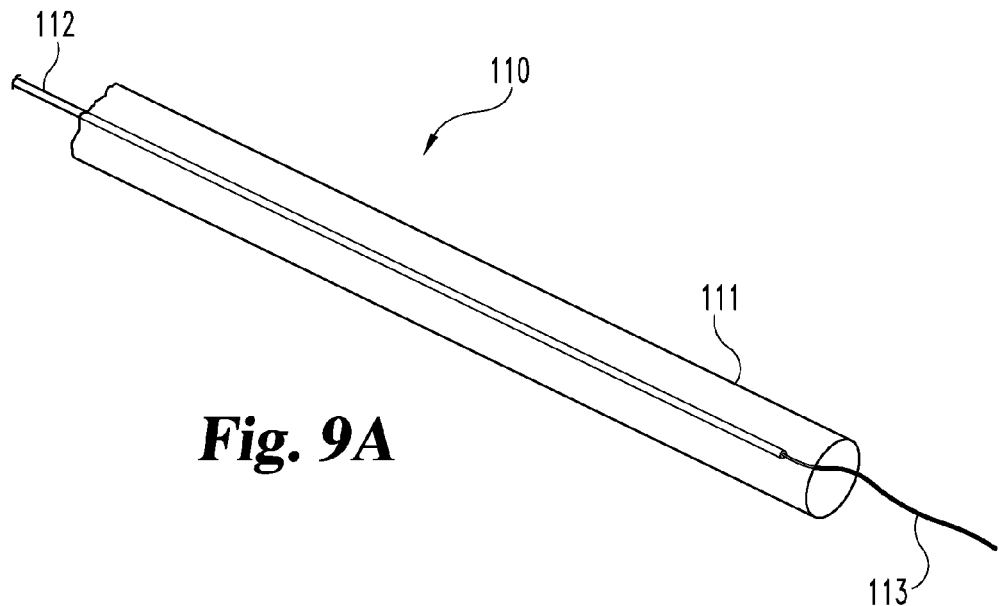
FIG. 9A is a perspective view of delivery instrument.
Figure 9B:
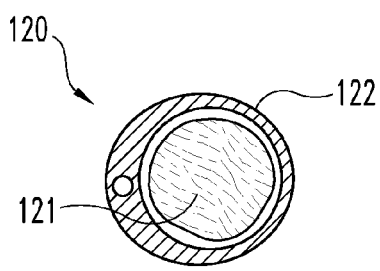
FIG. 9B is an end view of another delivery instrument.

In some instances, a delivery instrument that is capable of tracking along a suture of other guiding element will be used to deliver a material or substance (e.g., a plug body) to a bodily location. A variety of suitable instruments may be used in this regard. In some preferred forms, a delivery sheath will provide a lumen for carrying one or more plug bodies to a treatment site. Depending on the particular design, the guiding element may or may not pass through the plug-carrying lumen. When the guiding element also passes through the plug-carrying lumen, it may or may not pass through the plug material. In certain embodiments, the guiding element will not pass through the plug- or other material-carrying lumen, but instead will pass through another lumen (e.g., as in a bilumen sheath) or opening specifically incorporated onto or within the delivery instrument for receipt of a guide wire or the like. Referring now to FIG. 9A, shown is an illustrative delivery instrument 110 which includes a first lumen 111 for receipt of a fill substance or material, and a relatively smaller, second lumen 112 attached to the first lumen for receiving a guidewire 113 as shown. In some constructions, an optional cover or other shielding-type element will be incorporated over the leading end of first lumen 111. This sort of element can act to shield or otherwise protect the contents of the lumen while they travel to a treatment site, for example, in situations where there is moisture present at the treatment site and it is desirable for the contents to remain relatively dry prior to their full deployment. This cover-type device can then be caused or allowed to move aside or deform to allow the contents to be ejected or otherwise forced out of the lumen at the treatment site. FIG. 9B is an end view of another illustrative delivery instrument 120 that is somewhat similar to that shown in FIG. 9A except that the first lumen (shown carrying a fill substance 121) and the second lumen are seamlessly contained within the same housing 122. When the guiding element passes through its own separate passageway as in FIGS. 9A and 9B, a result is that a material or substance can be delivered to a treatment site with the aid of a guide wire without having the guide wire come into contact with the material or substance. This feature can be particularly useful in embodiments that involve the delivery of one or more plug or plug-type devices to a treatment site.

Figure 10:
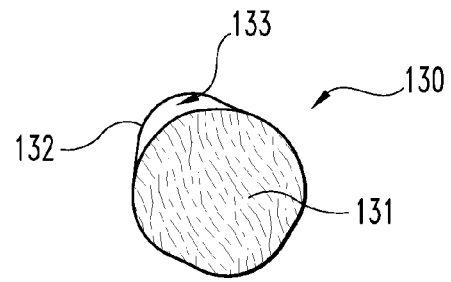
FIG. 10 is an end view of another inventive implantable device.

In some embodiments, a plug body will be configured for direct association with a suture of other guiding element, yet the specific construction will avoid having to pass the guiding element pass through a central region of the plug body. In some preferred forms, the guiding element will pass through the plug body but through a non-central region of the plug body. Illustratively, a lumen or opening proximate an exterior surface of a plug body may be formed during the initial construction of the plug body (e.g., when constructing a plug body in a mold), or it may be made subsequently by removing an amount of material from an already-formed plug so as to form a passageway through a peripheral region of the plug body. In some other preferred forms, a device (e.g., a sleeve, loop, etc.) providing its own opening or pathway for receipt of a guiding element will be attached to an exterior surface of the plug body. Still in some other preferred forms, an object will be incorporated onto the exterior surface of a plug body so that the object and the plug body when combined will form an opening or lumen for receipt of a guiding element. With reference now to FIG. 10, shown is an end view of an illustrative plug device 130 which includes a plug body 131 and a material layer 132 that is attached to the plug body. By virtue of this attachment, an opening 133 is formed along an exterior surface of the plug body for receipt of a wire guide or the like. Layers and other attachable objects and materials of various shapes and configurations may be used in this regard to form one or more suitable openings or passageway along an exterior surface of a plug body. In one illustrative construction technique, a material layer is rolled up to form a plug body, and an opening is formed in the plug between successive layers, for example, between an outermost layer and an underlying layer.

Figure 11:
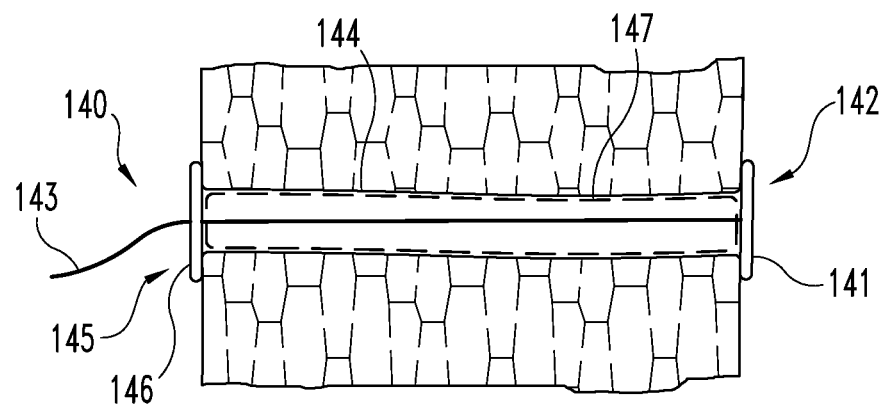
FIG. 11 shows another inventive medical system.

With reference now to FIG. 11, shown is a fistula treatment system 140 according to one embodiment of the present invention which includes a first anchoring member 141 deployed at a first fistula opening 142. A suture 143 extends from this member and through a fistula tract 144 toward a second fistula opening 145 where the suture is anchored to a second anchoring member 146. An optional fill material 147 can be delivered to the tract to occupy a substantial volume of the tract. In one specific illustrative method, the first anchoring member is deployed at the first opening and maintained there, e.g., by holding tension on it or by attaching it to tissue around the opening. Thereafter, multiple plugs or other bits or pieces of material, and potentially also one or more drugs or other active ingredients, are stuffed into the tract until it is essentially filled. The second anchoring member is then placed over the second opening and maintained there, e.g., by associating the suture with the second anchoring member so that a degree of tension can be generally held on the suture between the first and second anchoring members and/or by attaching the member to tissue in or around the second opening.

In some forms, an anchoring member and a passage-traversing member (e.g., a suture) will be specifically adapted to engage or otherwise physically interact with one another for providing at least a temporary connection between the two, whether this connection is fairly well fixed or whether it allows for some degree of play between the two components while still generally holding them together. Illustratively, an anchoring member may provide an opening through which an elongate element can be passed in a first direction, yet due to their relative constructions, the elongate element essentially will be unable to pass back through the opening. A variety of one-way only engagement mechanisms may be utilized in this regard. In some alternative forms, the elongate element will be able to pass back through the opening in the anchoring member but the force required to do so will be more than that experienced at the treatment site so that the two will remain in a generally fixed relationship at the treatment site even when subjected to forces that would attempt to undo this relationship.

Figure 12:
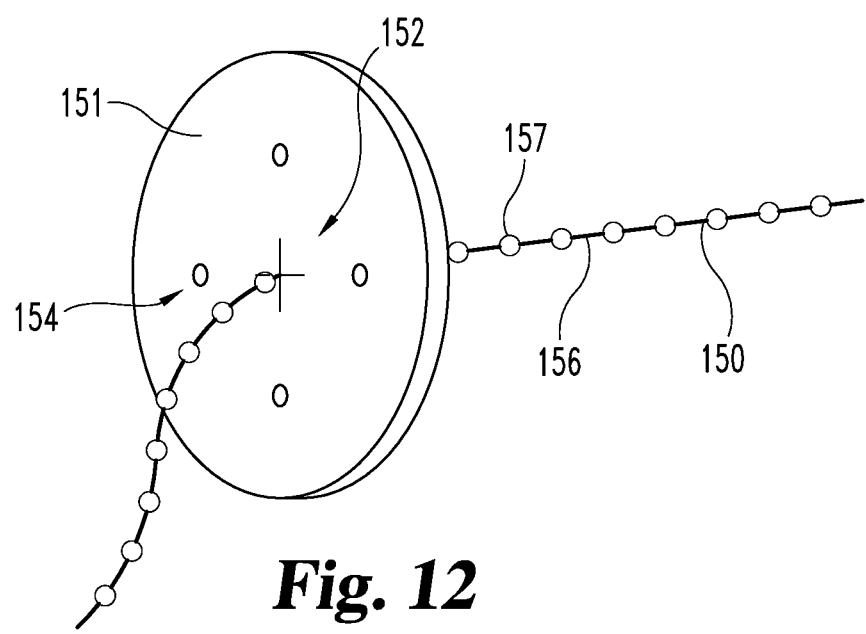
FIG. 12 is a partial view of a medical system according to one embodiment of the present invention.

With reference now to FIG. 12, shown is one illustrative manner in which an elongate element 150 and an anchoring member 151 can be made to engage one another for providing an adjustable connection between the two. A wall of the anchoring member provides an opening 152 through which the elongate element can be passed. While not necessary broader aspects of this feature, this particular opening is provided by a pair of crossed slits in the anchoring member wall. Optional holes 154 (e.g., for drainage) are also present in the anchoring member. Elongate element includes a main wire 156 as well as a plurality of enlarged portions 157 spaced along the wire which have cross sectional dimensions relatively larger than that of the main wire. By pulling the end of the elongate element with a certain degree of force, the enlarged portions can be forced through the opening one by one in a first direction. The opening and the enlarged portions can be shaped and configured in a variety of manners. Depending on the dimensions and other properties of the respective components, the degree of force required to advance an enlarged portion through the opening can vary. For example, a degree of force F may be required to pull an enlarged portion through the opening in a first direction, with this force F being somewhat higher than the forces expected at the treatment site attempted to pull the enlarged portion back through the opening.

Figure 13:
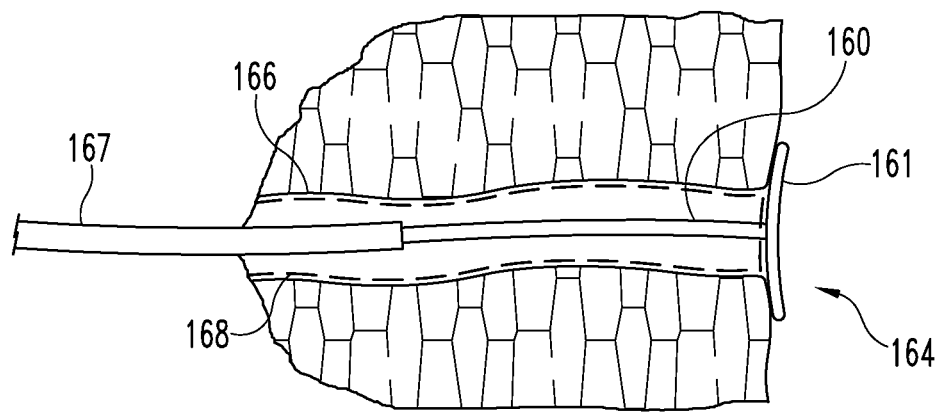
FIG. 13 is a partial view of another inventive medical system.

As discussed above, in some instances, a somewhat heftier elongate structure such as a generally solid biodegradable or non-biodegradable three-dimensional graft body will be made to extend through a bodily opening or passageway. Such a structure will generally have more heft and bulk than a conventional thread or filament. With reference now to FIG. 13, shown is an anchored elongate three-dimensional graft member 160 according to one inventive embodiment. In this illustrative arrangement the graft member is connected to, and extends away from, an anchoring body 161 that is positioned over a fistula opening 164. In doing so, the graft member extends through a fistula tract 166 and toward a second fistula opening (not shown). Anchoring body 161 might be any of those described herein. While not necessary to broader aspects of this embodiment, in certain illustrative modes of delivery where suitable access to fistula opening 164 can be obtained, the graft member 160 might be positioned in a delivery sheath 167, and a second end of the sheath (not shown) inserted into fistula opening 164 and advanced toward the second fistula opening. With anchoring body 161 contacting tissue adjacent fistula opening 164, the sheath can be further advanced and ultimately withdrawn from the tract through the second fistula opening so that graft member 160 becomes unsheathed and deployed within the fistula tract 166. Alternatively, such an anchored graft member could be delivered into the fistula tract in the opposite direction, for example, where the anchoring body is compressible or otherwise deformable so that it can be folded, rolled, collapsed and/or otherwise compacted to a lower-profile condition for traversing the tract whether wholly outside the sheath or fully or partially inside it.

Continuing with FIG. 13, while graft member 160 is generally cylindrical, such bodies can have a variety of shapes and configurations. Whether cylindrical or non-cylindrical, this sort of plug body or core-like member can, for example, have a general diameter of about 1.4 mm to about 8.0 mm and a length of about 0.5 cm to about 30 cm, although larger or smaller values for these dimensions can be used. A graft member in some forms of the invention will include a portion having a general diameter ranging from about 2.0 mm to about 7.0 mm, or from about 2.5 mm to about 6.0 mm, or from about 3.0 mm to about 5.3 mm, and a length ranging from about 2.0 cm to about 24.0 cm, or from about 3.0 cm to about 15.0 cm, or from about 4.0 cm to about 12.0 cm. In this specific illustrative embodiment, graft member 160 has little or no expandability in the fistula tract although graft members having a moderate or high degree of expandability will be utilized in some embodiments.

Such a graft member can have a constant or varying cross-sectional area along its length. Illustratively, a graft member, or any portion thereof, can exhibit a generally cylindrical shape, a conical shape or any other suitable shape including some that have tapered and/or non-tapered longitudinal portions. Thus, for example, graft member 160 instead could be tapered along its length in either direction. As well, a cross section of a particular portion of a graft member can exhibit a variety shapes including some that have rectilinear and/or curvilinear features. Thus, a graft member can include a portion having a generally circular or non-circular (e.g., elliptical, square, star-shaped, hexagonal, etc.) cross section. Additionally or alternatively, a graft member can include various other three-dimensional volumetric body portions such as but not limited to braids, tubes, hemi-cylinders, strands, threads, strips and other shaped body portions having suitable dimensions.

Such graft members and other implant components described herein can be formed with one or more of a variety of naturally derived and/or non-naturally derived materials, and they can be constructed in any suitable manner including but not limited to by extrusion, using a mold or form, formation around a mandrel, and/or combinations or variations thereof. In some embodiments, an implant body is formed with a reconstituted or otherwise reassembled ECM material such as a highly expandable ECM foam or sponge material. Implant bodies can also be formed by folding or rolling, or otherwise overlaying one or more portions of a biocompatible material, such as a biocompatible sheet material. The overlaid biocompatible sheet material can be compressed and dried or otherwise bonded into a volumetric shape such that a substantially unitary construct is formed. In some forms, an inventive implant component is constructed by randomly or regularly packing one or more pieces of single or multilayer ECM sheet material within a mold and thereafter processing the packed material.

Continuing with FIG. 13, the anchored graft member 160, which has a more slender cross sectional dimension relative to the fistula tract through which it extends, is capable of receiving an optional fill material 168 therealong in the tract. Fill material 168 can be or include a variety of biodegradable and/or non-biodegradable plug or plug-like members and/or other objects or materials as discussed elsewhere herein including flowable and non-flowable substances. When a conjunctive material such as fill material 168 is to accompany a graft element like graft member 160 in a bodily passageway, the order and manner in which the various components are delivered into the passageway can be varied to suit a particular application. Illustratively, a sheathed or unsheathed graft member might be positioned in a fistula tract first, and then subsequently a fill substance or object might be delivered into the tract alongside or around the sheathed or unsheathed graft member. In the latter case, for example, one or more plug bodies might be delivered into the tract over a sheathed plug. The sheath might be designed to remain in the tract indefinitely such as where a biodegradable sheath or sheath-like coating is employed. Where the sheath is designed for removal, the one or more plug bodies can be retained in the tract as the sheath is being withdrawn so as to deploy the one or more plug bodies in the tract directly over the graft member. Alternatively, a graft member and fill material might be delivered into a bodily passage in a generally simultaneous fashion. In some preferred forms, at least one of the graft member and the fill material, and possibly both of these components, will include a remodelable material such as a remodelable ECM material although other combinations of the materials discussed herein can be used.

Figure 14:
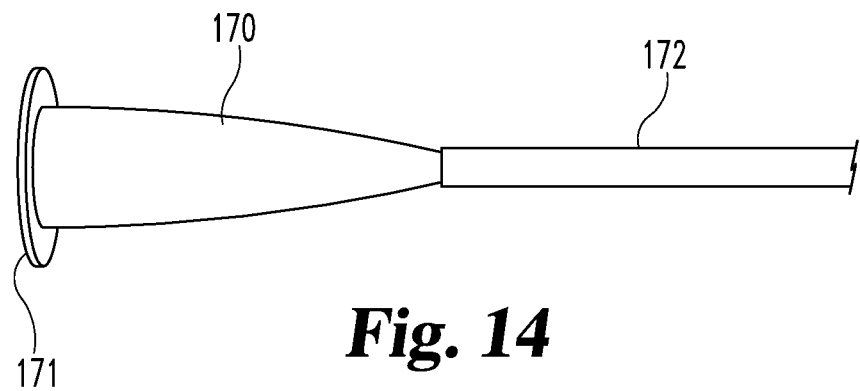
FIG. 14 is a partial view of still another inventive medical system.

FIG. 14 shows a graft member 170 which is similar to that shown in FIG. 13 except that it is formed with a rather highly expandable material such as a highly expandable ECM material. Constructing graft members with such materials allows for the use of ultra low-profile delivery sheaths while still providing graft members that, upon expanding, will be able to fill a substantial portion of a tortuous fistula passage or other bodily opening or passage including any pockets, crevices or other irregular-shaped spaces in and around an opening or passage. In many embodiments, the expanded dimensions of this sort of graft member will be made considerably greater than the dimensions of the opening or passage into which the member is intended to be deployed. The illustrated graft, which is shown connected to an optional anchoring body 171, too is capable of receiving an optional fill material therealong in a fistula tract or other bodily opening or passageway. In such embodiments, the order and manner in which the various components are delivered to the treatment location can be varied to suit a particular application. Illustratively, the graft member while inside a delivery sheath 172 can be positioned in a fistula tract with a fill material located alongside or around the sheath. With this sort of arrangement, for example, the sheathed member might be delivered to the tract first, and then one or more plug bodies might be delivered to the tract over the previously-placed sheath. Thereafter, the sheath might be removed while retaining the one or more plug bodies in the tract so as to deploy the one or more plug bodies in the tract directly over or alongside the highly expandable graft member. Whether caused to expand simply by being removed from the delivery sheath and/or upon contacting bodily fluids, injected saline, etc. at the treatment site, the graft member will expand inside the tract, and in doing so, will forcibly contact the surrounding fill material(s), e.g., so as to create a more snug fit of all the plug components within the tract.

When fully unsheathed, an expanded graft member like that shown in FIG. 14 can assume a variety of cylindrical and non-cylindrical shapes. In this regard, the graft member 170 might eventually reach a cylindrical shape upon full expansion in which case FIG. 14 illustrates the member in a partially expanded condition. Alternatively, graft member 170 might have more of a conical or tapered shape as shown in FIG. 14 upon full expansion. When a highly expandable graft member has a significant taper in an expanded condition, correspondingly there will be significant differences in density along the length of the plug when it is stuffed into a delivery device lumen having a generally constant diameter as shown in FIG. 14. Larger-diameter regions of the conical-like plug (i.e., those proximate anchoring body 171) will be more densely packed into the sheath's lumen than will smaller-diameter regions of the plug.

FIG. 15A shows a plug body 180 according to another embodiment of the present invention. Body 180 includes a rolled segment of a single or multilayered remodelable ECM sheet material 181. While not necessary to broader aspects of this embodiment, the formation of such a body might include rolling up an elongate rectangular strip of ECM material, or rolling up a larger sheet to form an lengthier cylindrical construct which can then be cut into multiple, smaller pieces. With this sort of construction which could additionally or alternatively include folded sheet portions, almost the entire perimeter edge of the ECM sheet remains exposed in the rolled plug body. In this particular illustrative construction, the opposing ends of the rolled segment each include a high concentration of the exposed ECM edges 182. Such remodelable ECM materials can be provided by collagenous materials obtained from a warm-blooded vertebrate, and especially a mammal. Remodelable ECM tissue materials harvested as intact sheets from a mammalian source and processed to remove cellular debris can be advantageously processed to retain at least a portion, and potentially all, of the native collagen microarchitecture of the source extracellular matrix. This matrix of collagen fibers provides a scaffold to facilitate and support tissue ingrowth, particularly in bioactive ECM implant materials, such as porcine small intestinal submucosa or SIS (Surgisis® Biodesign™, Cook Medical, Bloomington Ind.), that are processed to retain an effective level of growth factors and other bioactive constituents from the source tissue. In this regard, when an inventive construct incorporates this sort of material, cells will invade the remodelable material upon implantation eventually leading to the generation of newly-remodeled, functional tissue. FIG. 15B shows a rolled segment 185 similar to that shown in FIG. 15A except that the segment tapers off in a rounded fashion toward each of its ends.

Figure 16:
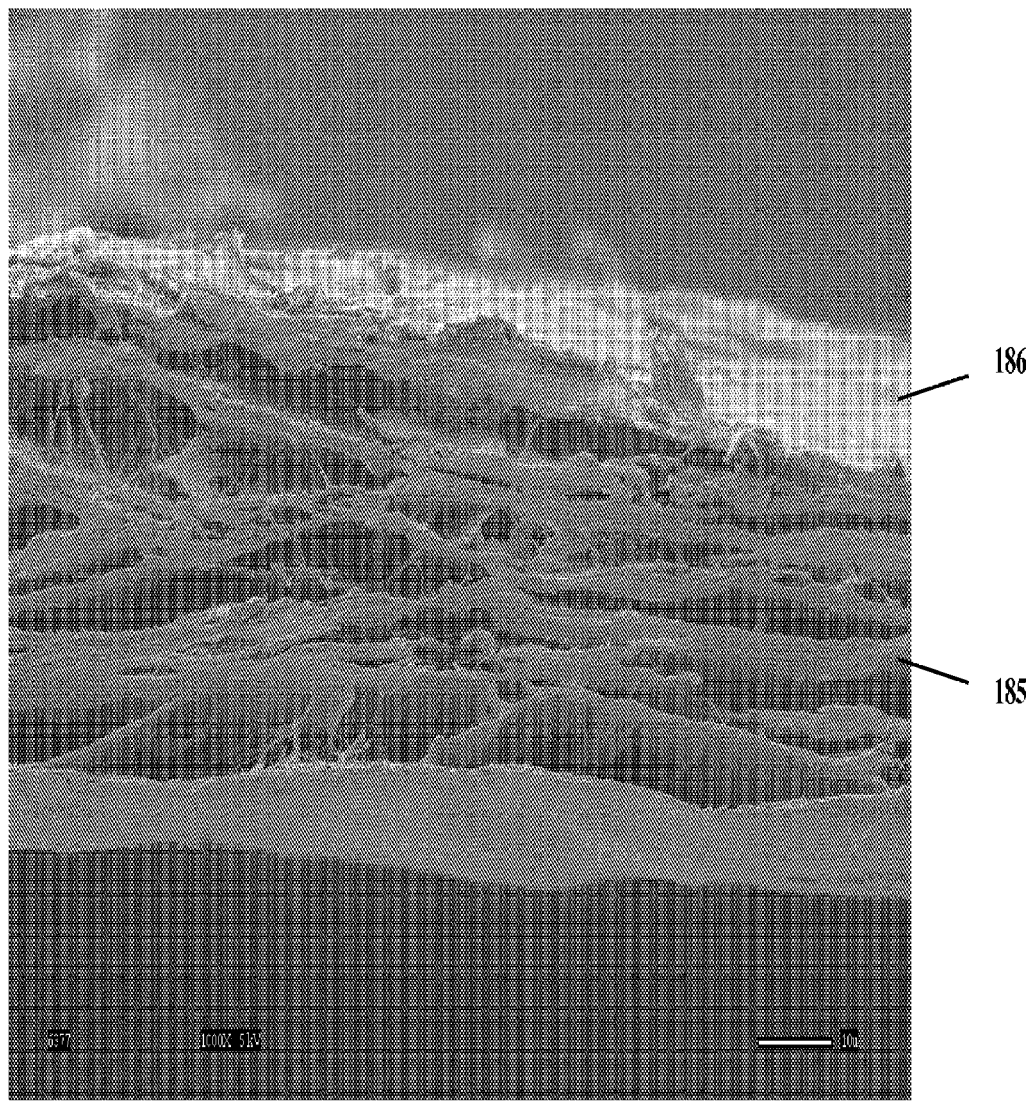
FIG. 16 is an image of a graft material useful in certain embodiments of the present invention.

FIG. 16 is a photomicrograph taken by scanning electron microscopy and shows an edge of a submucosal ECM material. As can be seen, the side edge 185 of the material has pockets and cavernous regions within the native microarchitecture which allows for the easy migration of cells into the inner regions of the matrix to promote integration of the graft material and wound healing. A less porous top surface 186 of the material can also been seen in the illustrative layer. The side edge provides an advantageous pathway for cells and other bodily substances to enter and populate the matrix, as opposed to the less porous and less inviting top and bottom surfaces. Moreover, the graft material can be processed to retain at least some of its native biologic components that effect cell response, including heparin sulfate, hyaluronic acid, and fibronectin. These materials, remaining in the graft, will even more advantageously promote migration and development of the cells when they are able to enter through the edge portions of the material.

If such ECM materials are used, for example, in the construction of a rolled, folded, etc. segment, e.g., like that shown in FIG. 15, it becomes apparent that a significant portion of the exterior surface of the resulting plug body will be quite densely packed with exposed edge portions of the ECM material. The numerous exposed ECM edges will provide an abundance of openings and passages for cells and other bodily substances to easily enter the microarchitectures of the ECM materials, and once in, the bioactive agents retained in the matrices will induce migration and proliferation of the cells within and between the individual layers so as to promote integration and replacement of the layers, and of the plug body as a whole, with newly-remodeled patient tissue.

In alternative embodiments, a graft body like that shown in FIG. 15A will incorporate more than one layer of material, for example, constructs with rolled, folded or otherwise situated layers. Any two layers or sheets within a single construct can be formed with the same or different materials. In some instances, two layers might initially be similar (e.g., two ECM layers) but one layer will be physically, chemically, biologically and/or otherwise modified relative to the other. Accordingly, specific types of layers can be located at particular locations within a construct, and in this regard, the location of a particular sheet or layer might be selected based on advantages expected to result from having that layer reside at that location at the eventual treatment site (e.g., at or near an interior or exterior part of the body). As one example, layers within a single graft body can have different densities, rates of degradation, degrees of stiffness, resistances to hydration, abilities to withstand exposures to certain substances at an implant site, and/or can be different with respect to any other quality including being coated with or otherwise incorporating one or more substances such as drugs (antimicrobial, anti-inflammatory, etc.), bioactive substances, radiopaque components and/or other substances as described elsewhere herein. Illustratively, a graft might include some layers that are formed with a naturally derived material such as a harvested ECM material and other layers that are formed with a non-naturally derived material such as a biodegradable synthetic polymeric material.

Referring now to FIG. 17, shown is an illustrative treatment product that includes multiple plug bodies 180 from FIG. 15A positioned along an anchored suture line 190. The suture line is connected to, and extends away from, an anchoring body 192 that is positioned over a fistula opening 193. In some embodiments, this sort of multi-body graft product plug will be formed prior to delivering the product to an implant site, and in these instances, the plug bodies may or may not be directly connected to one another. Such a multi-body graft product can be enclosed within sterile medical packaging. The plug bodies will be loosely held together along suture line 190 in some constructions. In one preferred embodiment, the suture line 190 will be knotted off between each plug body so as to allow the technician to cut the strand to length while retaining the desired number of plug bodies along the remaining length of suture. In some other forms, a strand arrangement like that shown in FIG. 17 will be formed, at least in part, at the implant site. Illustratively, the suture line 190 might be positioned in a fistula tract and thereafter plug bodies, or a separate delivery instrument specifically adapted to carry such plug bodies and track along the suture line, will be delivered into the tract. By having such a plurality of segments oriented in this fashion and closely packed together along the tract, a significant amount of edge material is exposed within the tract generally facing the interior walls of the tract. The material of the rolled segments is generally rolled in the direction of the fistula tract such that the opposing ends of the segment are positioned generally transverse to the longitudinal direction of the fistula tract. Such an arrangement provides a significantly greater amount of exposed ECM edges along the tract than would an elongate rolled plug having a longitudinal axis extending along the longitudinal axis of the fistula tract or other bodily passageway. This sort of strand can include any suitable number of segments, and there can be multiple strands placed along a bodily passageway or tract.

Figure 19:
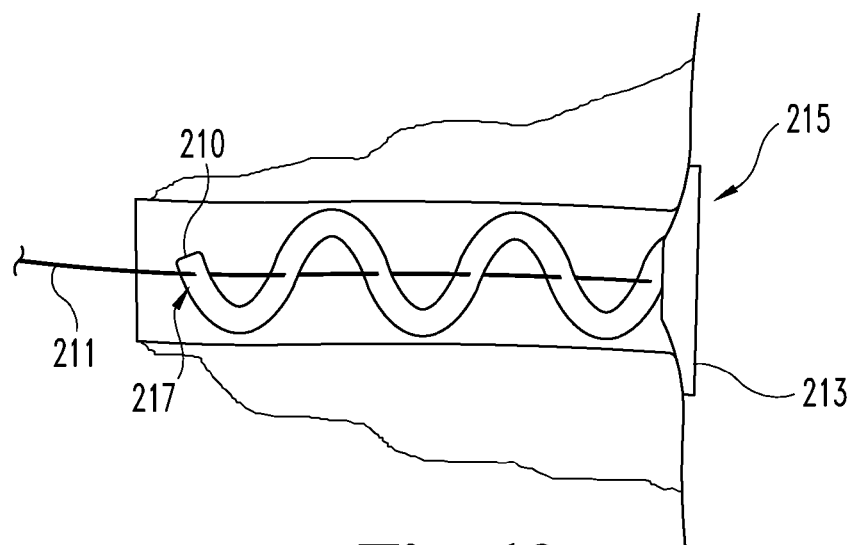
FIG. 19 is a side view of an implantable device according to another embodiment of the present invention.

FIG. 19 shows an inventive product that includes an elongate, deformable plug body 210 with an elongate suture 211 threaded through the plug body in multiple locations along the plug body. The plug body 210 is formed with an extracellular matrix material and is generally cylindrical although it could be shaped and configured in a variety of manners and could be formed with one or more of a variety of biocompatible materials as described herein. In this particular illustrative embodiment, the suture is anchored to an optional anchoring member 213, and from this member, extends toward a secondary fistula opening (not shown). Anchoring member 210 is positioned over a primary fistula opening 215, and in some instances, will be useful to block or seal off the primary opening. Multiple passages 217, which extend in a generally lateral direction through the plug body, are spaced along the length of the plug body. Various patterns and arrangements of passages can be employed such that any passage can be placed at any suitable location along the plug body. By threading the suture through the various passages back and forth along the plug body, force can be applied to the deformable plug body to cause it to scrunch up along the suture in the fistula tract as generally shown. Longitudinally compressing the plug in this manner, which in turn causes portion of the plug to expand laterally outward in the tract, can be useful for filling irregular shaped spaces and regions within a fistula or other bodily passageway or opening. Multiple such plug bodies can be threaded over a single suture.

Turning now to a more detailed discussion of materials that can be utilized in the present invention, as discussed elsewhere herein, inventive constructs can incorporate naturally derived and/or non-naturally derived materials. In this regard, one or more components of an inventive construct may comprise one or more of a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), poly-dioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethyl carbonate), poly(iminocarbonate), copoly(ether-esters) (e.g., PEO/PLA), polyalkylene oxalates, and polyphosphazenes. These or other bioresorbable materials may be used, for example, where only a temporary function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and poly-caprolactam; alkyd resins, polycarbonates; polyoxymethylenes; polyimides; polyethers; epoxy resins, polyurethanes; rayon; and rayon-triacetate.

As well, inventive constructs can incorporate biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

In certain embodiments, one or more device components will be comprised of a remodelable material. Particular advantage can be provided by devices that incorporate a remodelable collagenous material. Such remodelable collagenous materials, whether reconstituted or naturally-derived, can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth on, around, and/or in bodily regions in which inventive devices are implanted or engrafted.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Submucosa-containing or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa-containing or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Inventive devices can incorporate xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

In certain forms, inventive devices include a material receptive to tissue ingrowth. Upon deployment of such devices in accordance with the present invention, cells from the patient can infiltrate the material, leading to, for example, new tissue growth on, around, and/or within the device. In some embodiments, the device comprises a remodelable material. In these embodiments, the remodelable material promotes and/or facilitates the formation of new tissue, and is capable of being broken down and replaced by new tissue. Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

In this regard, any component of a medical graft product of the invention (including any ECM material) can have a level or degree of porosity. In certain embodiments, the porosity of a layer of ECM material is lowered by drying the material under compression. In general, compressing a pliable open matrix material, such as a pliable ECM material, increases the material's bulk density and decreases the material's porosity by decreasing the size of the voids in the open matrix. As is the case in certain aspects of the invention, when such a material is dried while being compressed, particularly under vacuum pressing conditions, the open matrix structure can become somewhat fixed in this relatively higher bulk density, lower porosity state (i.e., in a relatively more collapsed state). It should be noted that different compressing and drying techniques and/or methods, including different degrees of compressing and drying, can be designed through routine experimentation so as to allow for a material layer having an optimal degree of material bulk density and/or porosity for a particular application or procedure.

It is sometimes advantageous to perform drying operations under relatively mild temperature exposure conditions that minimize deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

Turning now to a discussion of three-dimensionally stable materials that can be incorporated into inventive grafts, and components thereof (e.g., plug bodies 70, graft member 160, fill material 168, etc.), in accordance with some aspects of the present invention, such materials may include any suitable biocompatible sponge or foam material. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers. More preferred sponge compositions of the invention will comprise collagen as a matrix-forming material, either alone or in combination with one or more other matrix forming materials. In general, sponge matrices useful in embodiments of the invention can be formed by providing a liquid solution or suspension of a matrix-forming material, and causing the material to form a porous three-dimensionally stable structure; however, a sponge or foam material can be formed using any suitable formation method, as is known in the art.

Illustratively, in the formation of a collagenous sponge or foam material, a collagen solution or suspension can be prepared. The collagen may be derived from mammalian or other animal sources, for example, bovine, porcine or human sources, and desirably is derived from remodelable ECM materials as discussed herein. Synthetically-derived collagen may also be used. The determination of suitable collagen concentrations in the solution will be within the purview of those skilled in the art, with concentration ranges of about 0.05 g/ml to about 0.2 g/ml being typical.

Digestion of the collagen to form the collagen solution is usually carried out under acidic conditions, starting with ground, minced or otherwise comminuted collagen-containing tissue. Optionally, enzymatic digestion may be utilized using known enzymes for this purpose such as pepsin, trypsin, and/or papain. After digestion, the enzymes can be removed by suitable, known techniques.

The collagenous solution and/or suspension can be employed as a moldable or castable material in the formation of the foam or sponge. The cast material can be dried directly without chemical crosslinking or can be crosslinked with a suitable crosslinking agent and then dried. Illustrative crosslinking agents for these purposes include glutaraldehyde, formaldehyde, carbodiimides, UV irradiation, or other crosslinking agents. In preferred embodiments of the invention, the crosslinking agent will contain polar groups that impart a hydrophilic character to the final sponge matrix material. Desirably, a polyepoxide crosslinker is utilized for this purpose, especially a polyglycidyl ether compound. Suitable such compounds include ethylene glycol diglycidyl ether, available under the trade name Denacol EX810 from Nagese Chemical Co., Osaka, Japan, and glycerol polyglycidyl ether available under the trade name Denacol EX313 also from Nagese Chemical Co. Typically, polyglycidyl ethers or other polyepoxide compounds utilized in the invention will have from 2 to about 10 epoxide groups per molecule. The use of such epoxides and/or other crosslinking agents which impart polar groups and a hydrophilic character to the resulting matrix will provide for good wetability and rapid hydration and expansion of closure devices of the invention.

Preferred sources of collagen for forming sponge matrices include extracellular matrix materials as discussed above, such as collagenous submucosal tissues, and other collagenous basement membrane materials. These include, for example, small intestinal submucosa, stomach submucosa, urinary bladder submucosa, liver basement membrane, and other basement membrane materials. For additional information as to these collagenous matrix materials and their preparation, reference can be made for example to U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety. In forming sponge matrices, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

Sponge matrix materials can be highly expandable when wetted, so as to achieve an expanded configuration. Illustratively, expandable sponge materials can exhibit the capacity to expand at least 100% by volume, more preferably at least about 200% by volume, and typically in the range of about 300% by volume to about 1000% by volume, when wetted to saturation with deionized water. Sponge materials used in the invention can also exhibit advantageous rates of expansion, achieving volume expansions as noted above in less than about 10 seconds, more preferably less than about 5 seconds, when immersed in deionized water.

Highly compact, dense sponge matrices can be prepared by first hydrating or otherwise wetting a porous sponge matrix, and then compressing and drying the element. Such preparative processes generally provide a more dense, rigid and stably compressed sponge matrix than processes such as simple compaction of the dry sponge matrix. Drying can be conducted sufficiently to stabilize the sponge matrix. For example, preferred drying procedures will reduce the liquid (e.g. water) content of the matrix to less than about 20% by weight, more preferably less than about 10% by weight. Compression forces can be applied so as to achieve a final density and/or desirable configuration, and can be applied in one, two or three dimensions, including radially. The drying of the compacted element can involve lyophilization (or freeze drying) or vacuum drying at ambient or elevated temperatures. When processed in this fashion, upon removal of the compaction force, the sponge matrix is stabilized structurally and remains in its highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

Compressed sponge matrices forming graft bodies can be highly dense, typically having densities of at least about 0.05 g/cm3, preferably in the range of about 0.05 g/cm3 to about 0.2 g/cm3, and more preferably about 0.075 g/cm3 to about 0.2 g/cm3. The compacted sponge matrix can have sufficient rigidity to be deployed by passage through bodily vessels, needles, catheters or sheaths, such as by utilizing a push rod or other pusher element to force the sponge matrix body through the needle and/or catheter cannula for example. Expanded sponge densities (dry) will generally be less than the corresponding compacted densities. Typical expanded densities (dry) will range from about 0.01 g/cm3 to about 0.1 g/cm3, more preferably about 0.02 g/cm3 to about 0.07 g/cm3.

Compressed sponge materials may also contain agents which promote further retention of the compressed, high density form of the matrices. These may include for example starch, cellulose, sugars such as dextrose, or glycerin. Such agents can optionally be included in the liquid (preferably aqueous) used to hydrate or otherwise wet the sponge prior to compaction and drying. For additional information concerning foam or sponge form materials that can be useful in embodiments of the invention, reference can be made, for example, to U.S. Pat. App. Pub. No. 2003/0013989.

In additional embodiments, graft elements useful in the invention can be made from ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a bodily segment within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of three-dimensionally stable shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded collagenous material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression.

Expanded collagenous materials can be used to prepare a wide variety of graft elements useful in certain inventive devices. Methods for preparing such elements can include contacting an ECM or other collagenous starting material with an alkaline substance in an amount effective to expand the material, casting or otherwise forming the expanded collagenous material into a particular shape (e.g. an elongate tube or cylinder or a plug-like segment), and lyophilizing the expanded material to form a dried graft body.

Products and methods of the invention can be used to treat a variety of fistulae and other passages and openings in the body. In some preferred aspects, products and methods are adapted for treating fistulae having at least a primary opening and a fistula tract extending therefrom, for example, a primary opening in the alimentary canal. Some fistulae to be treated will have at least a first fistula opening, a second fistula opening and a fistula tract extending therebetween. In this context, the term "fistula tract" is meant to include, but is not limited to, a void in soft tissues extending from a primary fistula opening, whether blind-ending or leading to one or more secondary fistula openings, for example, to include what are generally described as simple and complex fistulae.

In this regard, inventive products and methods may be useful to treat urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae. Inventive products and methods can be used to treat a fistula regardless of its size and shape, and in some forms, are utilized to treat a fistula having a primary opening, secondary opening, and/or fistula tract with a diameter ranging from about 1 millimeter to about 20 millimeters, more typically from about 5 millimeters to about 10 millimeters.

Additionally, inventive products and methods can be used to occlude, block, fill, plug and/or otherwise treat a variety of vascular (e.g., arterial, venous, etc.) and non-vascular openings and passageways in the body. In some instances, an inventive device will be configured for placement in a naturally occurring location in the body, for example, in a native lumen or other open space in a bodily system, e.g., in an organ or other component of the circulatory, respiratory, digestive, urinary and reproductive, sensory, or endocrine systems. In certain aspects, a space to be occupied by an inventive graft is one that exists naturally in the body but relates to a disease, defect, deformation, etc. Alternatively, an opening or passageway to be occupied might be one resulting from an intentional or unintentional trauma to the body including but not limited to some relating to vehicular accidents, gunshots and other similar wounds, etc., as well as some resulting from the passage of a medical instrument (e.g., a needle, trocar, etc.) through cutaneous, subcutaneous, and/or intracutaneous tissue.

Additionally, an implantable component can include one or more radiopaque and/or ecogenic markers or a radiopaque coating or impregnation to assist in visualization of the component during a procedure. For example, radiopaque substances containing tantalum, barium, iodine, or bismuth, e.g. in powder form, can be coated upon or incorporated within an anchoring member or fill material, such that, for example, the location of the anchoring member or fill material within a patient's body can be detected.

The present invention also provides, in certain aspects, a line of medical products, wherein a medical product of the invention includes one or more devices, apparatuses or systems of the invention in a sealed package. In some forms of the invention, medical products are provided that include one or more inventive devices or systems enclosed within sterile medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A method for treating a fistula having first opening, a second opening and a fistula tract having a fistula tract wall extending therebetween, the method comprising:
    providing an anchored three-dimensional graft member proximate the first fistula opening and extending therefrom through the fistula tract toward the second fistula opening, the anchored three-dimensional graft member capable of receiving one or more plug bodies therealong for filling a substantial portion of the tract; and
    inserting one or more plug bodies through the second opening, along the anchored three-dimensional graft member and into the fistula tract, wherein the one or more plug bodies comprise rolled or folded sheet material, wherein the one or more plug bodies each include a first end face and a second end face opposite the first end face, wherein the first end face and the second end face each present a plurality of exposed edges of the rolled or folded sheet material; and
    further wherein during said inserting, the first end face and the second end face of the one or more plug bodies are oriented transverse to a longitudinal axis of the fistula tract so as to face toward the fistula tract wall.

2. The method of claim 1, wherein said anchored three-dimensional graft member has a diameter in the range of about 2 mm to about 7 mm.

3. The method of claim 1, wherein said anchored three-dimensional graft member comprises an ECM material.

4. The method of claim 3, further comprising delivering an ECM fill material into the fistula tract around the anchored three-dimensional graft member.

5. The method of claim 1, wherein said providing includes deploying an anchoring member proximate the first fistula opening, the anchored three-dimensional graft member connected to and extending from the anchoring member.

6. The method of claim 5, wherein said deploying includes said anchoring member urging the first fistula opening toward a closed position.

7. The method of claim 5, wherein said anchoring member comprises a fillable body.

8. The method of claim 1, further comprising injecting a flowable material into the fistula tract.

9. The method of claim 1, wherein said plug body comprises a volumetrically expandable material.

10. The method of claim 1, further comprising delivering two or more of said plug bodies into the fistula tract over the anchored three-dimensional graft member.

11. The method of claim 10, wherein said two or more plug bodies includes a first plug body and a second plug body having substantially the same dimensions.

12. The method of claim 10, wherein said two or more plug bodies includes a first plug body formed with a first material and a second plug body formed with a second material.

13. The method of claim 1, wherein said anchored three-dimensional graft member comprises an expandable material.

14. The method of claim 13, further comprising positioning two or more of said plug bodies in the fistula tract over the three-dimensional graft member.

15. The method of claim 1, wherein the sheet material comprises an extracellular matrix sheet material.

16. The method of claim 15, wherein the extracellular matrix sheet material comprises growth factors retained from a source tissue for the sheet material.

17. The method of claim 16, wherein the extracellular matrix sheet material retains at least a portion of a collagen microarchitecture of a source tissue for the sheet material.

18. The method of claim 17, wherein the one or more plug bodies are cylindrical plug bodies having a cylindrical side wall extending between said first end face and said second end face.

19. The method of claim 15, wherein the extracellular matrix sheet material retains at least a portion of a collagen microarchitecture of a source tissue for the sheet material.

20. The method of claim 1, wherein the one or more plug bodies are cylindrical plug bodies having a cylindrical side wall extending between said first end face and said second end face.

21. A method for treating a void extending through soft tissue of a patient, the void including a first opening, a second opening and a passageway having a passageway wall extending therebetween, the method comprising:
    providing an elongate three-dimensional graft member extending through the passageway;
    advancing one or more plug bodies through the second opening and over the graft member to fill a substantial portion of the passageway, wherein the one or more plug bodies comprise rolled or folded sheet material, wherein the one or more plug bodies each include a first end face and a second end face opposite the first end face, wherein the first end face and the second end face each present a plurality of exposed edges of the rolled or folded sheet material; and
    further wherein during said advancing, the first end face and the second end face of the one or more plug bodies are oriented transverse to a longitudinal axis of the passageway so as to face toward the passageway wall.

22. The method of claim 21, wherein said advancing comprises advancing at least two of said plug bodies over the graft member.

23. The method of claim 21, wherein said one or more plug bodies includes a first plug body and a second plug body having different lengths.

24. The method of claim 21, wherein the sheet material comprises an extracellular matrix sheet material.

25. The method of claim 24, wherein the extracellular matrix sheet material comprises growth factors retained from a source tissue for the sheet material.

26. The method of claim 25, wherein the extracellular matrix sheet material retains at least a portion of a collagen microarchitecture of a source tissue for the sheet material.

27. The method of claim 26, wherein the one or more plug bodies are cylindrical plug bodies having a cylindrical side wall extending between said first end face and said second end face.

28. The method of claim 24, wherein the extracellular matrix sheet material retains at least a portion of a collagen microarchitecture of a source tissue for the sheet material.

29. The method of claim 21, wherein the one or more plug bodies are cylindrical plug bodies having a cylindrical side wall extending between said first end face and said second end face.

* * * * *